United States Patent
Kobus et al.

(10) Patent No.: US 10,877,041 B2
(45) Date of Patent: Dec. 29, 2020

(54) METHODS OF DETECTING BIOLOGICAL PRINTS, FLUIDS OR ANALYTES THEREIN USING POROUS SEMICONDUCTOR SUBSTRATES

(71) Applicant: Nicolas H. Voelcker, Blackwood (AU)

(72) Inventors: Hilton Kobus, Beaumont (AU); Taryn Guinan, Oaklands Park (AU); Nicolas H. Voelcker, Blackwood (AU); Ove Johan Ragnar Gustafsson, Mawson Lakes (AU); Hazem Hussein Soliman Abdelmaksoud, Mawson Lakes (AU)

(73) Assignee: Nicolas H. Voelcker

( * ) Notice: Subject to any disclaimer, the term of this patent is extended or adjusted under 35 U.S.C. 154(b) by 306 days.

(21) Appl. No.: 15/309,063

(22) PCT Filed: May 5, 2015

(86) PCT No.: PCT/AU2015/000263
§ 371 (c)(1),
(2) Date: Nov. 4, 2016

(87) PCT Pub. No.: WO2015/168724
PCT Pub. Date: Nov. 12, 2015

(65) Prior Publication Data
US 2017/0074885 A1    Mar. 16, 2017

(30) Foreign Application Priority Data
May 5, 2014  (AU) ................................ 2014901629

(51) Int. Cl.
*G01N 33/58*  (2006.01)
*A61B 5/1171*  (2016.01)
(Continued)

(52) U.S. Cl.
CPC .......... *G01N 33/585* (2013.01); *A61B 5/1171* (2016.02); *A61B 5/1172* (2013.01);
(Continued)

(58) Field of Classification Search
CPC .. G01N 33/585; G01N 33/94; G01N 21/6428; G01N 21/6456; G01N 21/6458;
(Continued)

(56) References Cited

U.S. PATENT DOCUMENTS 6,794,196 B2 * 9/2004 Fonash ................. B81C 1/0038
435/287.1
8,026,328 B2   9/2011 Rowell
(Continued)

FOREIGN PATENT DOCUMENTS

CN    101477058    6/2011
CN    101792147    5/2012
(Continued)

OTHER PUBLICATIONS

Seino, Teruyuki, et al. "Matrix-free laser desorption/ionization-mass spectrometry using self-assembled germanium nanodots." Analytical chemistry 79.13 (2007): 4827-4832.*
(Continued)

*Primary Examiner* — Robert J Eom
(74) *Attorney, Agent, or Firm* — Sheridan Ross P.C.

(57) ABSTRACT

The present disclosure provides methods for detecting biological print(s) or biological fluid(s) or target low molecular weight analyte(s) therein comprising contacting the suspected print(s) or fluid(s) with porous semiconductor substrates or microparticles (MPs) under conditions to allow said semiconductor substrates or microparticles to adhere to the print(s) or fluid(s) or analyte(s) therein, and analysing the adhered porous semiconductor substrates or MPs to detect the print(s), fluid(s) or analytes when present. The disclosure
(Continued)

also includes method for making porous semiconductor substrates.

5 Claims, 17 Drawing Sheets

(51) Int. Cl.
| | |
|---|---|
| *G01N 33/94* | (2006.01) |
| *G06K 9/00* | (2006.01) |
| *G01N 21/64* | (2006.01) |
| *C01B 33/02* | (2006.01) |
| *A61B 5/1172* | (2016.01) |
| *H01J 49/16* | (2006.01) |

(52) U.S. Cl.
CPC ......... *C01B 33/02* (2013.01); *G01N 21/6428* (2013.01); *G01N 21/6456* (2013.01); *G01N 21/6458* (2013.01); *G01N 33/94* (2013.01); *G06K 9/00006* (2013.01); *G06K 9/00013* (2013.01); *G01N 2021/6439* (2013.01); *H01J 49/161* (2013.01)

(58) Field of Classification Search
CPC .......... G01N 2021/6439; A61B 5/1171; A61B 5/1172; A61B 5/117; C01B 33/02; G06K 9/00006; G06K 9/00013; H01J 49/16; H01J 49/161; H01J 49/162; H01J 49/164
See application file for complete search history.

(56) References Cited

U.S. PATENT DOCUMENTS

2007/0224697 A1\* 9/2007 Park ................... H01J 49/0418
436/173
2012/0014858 A1 1/2012 Rowell

FOREIGN PATENT DOCUMENTS

| EP | 1919361 | 3/2014 |
|---|---|---|
| RU | 2417239 | 4/2011 |
| WO | WO 2007/017701 | 2/2007 |
| WO | WO 2007/120248 | 10/2007 |

OTHER PUBLICATIONS

Sato, Hiroaki, et al. "Surface cleaning of germanium nanodot ionization substrate for surface-assisted laser desorption/ionization mass spectrometry." Rapid Communications in Mass Spectrometry: An International Journal Devoted to the Rapid Dissemination of Up-to-the-Minute Research in Mass Spectrometry 23.5 (2009).\*
Guinan et al. "Rapid detection of illicit drugs in neat saliva using desorption/ionization on porous silicon," Talanta, 2012, vol. 99, pp. 791-798.
Kiraly et al. "Multifunctional porous silicon nanopillar arrays: antireflection, superhydrophobicity, photoluminescence, and surface-enhanced Raman scattering (SERS)," Nanotechnology, Jun. 2013, vol. 24, No. 24, 245704, 19 pages.
Lewis et al. "Desorption/ionization on silicon (DIOS) mass spectrometry: background and applications," International Journal of Mass Spectrometry, 2003, vol. 226, pp. 107-116.
Lowe et al. "Rapid drug detection in oral samples by porous silicon assisted laser desorption/ionization mass spectrometry," Rapid Communications in Mass Spectrometry, 2009, vol. 23, pp. 3543-3548.
Mcinnes et al. "Porous silicon-based nanostructured microparticles as degradable supports for solid-phase synthesis and release of oligonucleotides," Nanoscale Research Letters, 2012, vol. 7:385, 10 pages.
Wei et al. "Desorption-ionization mass spectrometry on porous silicon," Nature, May 1999, vol. 399, pp. 243-246.

International Search Report and Written Opinion prepared by the Australian Patent Office dated Jul. 20, 2015, for International Application No. PCT/AU2015/000263.
Agrawal et al. "Bare silica nanoparticles as concentrating and affinity probes for rapid analysis of aminothiols, lysozyme and peptide mixtures using atmospheric-pressure matrix-assisted laser desorption/ionization ion trap and matrix-assisted laser desorption/ionization time-of-flight mass spectrometry," Rapid Communications In Mass Spectrometry, 2008, vol. 22, pp. 283-290.
Baumann et al. "Standardized Approach to Proteome Profiling of Human Serum Based on Magnetic Bead Separation and Matrix-Assisted Laser Desorption/Ionization Time-of-Flight Mass Spectrometry," Clinical Chemistry, 2005, vol. 51, No. 6, pp. 973-980.
Chazalviel et al. "An Interface-Free-Energy Approach to Semiconductor Electrode Chemistry: Examples of Si and Ge," Journal of the Electrochemical Society, 2004, vol. 151, No. 2, pp. E51-E55.
Chen et al. "Affinity-based mass spectrometry using magnetic iron oxide particles as the matrix and concentrating probes for SALDI MS analysis of peptides and proteins," Analytical and Bioanalytical Chemistry, 2006, vol. 386, pp. 699-704.
Chiappini et al. "Biodegradable Porous Silicon Barcode Nanowires with Defined Geometry," Advanced Functional Materials, 2010, vol. 20, pp. 2231-2239.
Cooper et al. "Guidelines for European workplace drug testing in oral fluid," Drug Testing and Analysis, 2011, vol. 3, pp. 269-276.
Fang et al. "Electrochemical pore etching in Ge—An overview," Physica Status Solidi A, vol. 204, No. 5, pp. 1292-1296.
Finkel et al. "Ordered Silicon Nanocavity Arrays in Surface-Assisted Desorption/Ionization Mass Spectrometry," Analytical Chemistry, Feb. 2005, vol. 77, No. 4, pp. 1088-1095.
Gu et al. "Magnetic Luminescent Porous Silicon Microparticles for Localized Delivery of Molecular Drug Payloads," Small, Nov. 2010, vol. 6, No. 22, pp. 2546-2552.
Guinan et al. "Direct Detection of Illicit Drugs from Saliva Using Porous Silicon Microparticle Laser Desorption/Ionization Mass Spectrometry," PSST Conference Abstracts, Jan. 31, 2014, pp. 148-149.
Huang et al. "Metal-Assisted Chemical Etching of Silicon: A Review," Advanced Materials, 2011, vol. 23, pp. 285-308.
Kailasa et al. "Comparison of ZnS Semiconductor Nanoparticles Capped with Various Functional Groups as the Matrix and Affinity Probes for Rapid Analysis of Cyclodextrins and Proteins in Surface-Assisted Laser Desorption/Ionization Time-of-Flight Mass Spectrometry," Analytical Chemistry, Dec. 2008, vol. 80, No. 24, pp. 9681-9688.
Massad-Ivanir et al. "Optical Detection of *E. coli* Bacteria by Mesoporous Silicon Biosensors," Journal of Visualized Experiments, Nov. 2013, vol. 81, e50805, 8 pages.
Northen et al. "High Surface Area of Porous Silicon Drives Desorption of Intact Molecules," Journal of the American Society for Mass Spectrometry, Nov. 2007, vol. 18, No. 11, pp. 1945-1949.
Okuno et al. "Requirements for Laser-Induced Desorption/Ionization on Submicrometer Structures," Analytical Chemistry, Aug. 2005, vol. 77, No. 16, pp. 5364-5369.
Piret et al. "Matrix-Free Laser Desorption/Ionization Mass Spectrometry on Silicon Nanowire Arrays Prepared by Chemical Etching of Crystalline Silicon," Langmuir, 2010, vol. 26, No. 2, pp. 1354-1361.
Ramiro-Manzono et al. "Porous silicon microcavities: synthesis, characterization, and application to photonic barcode devices," Nanoscale Research Letters, 2012, vol. 7, 497, 6 pages.
Ronci et al. "Mass Spectrometry Imaging on Porous Silicon: Investigating the Distribution of Bioactives in Marine Mollusc Tissues," Analytical Chemistry, 2012, vol. 84, pp. 8996-9001.
Shen et al. "Porous Silicon as a Versatile Platform for Laser Desorption/Ionization Mass Spectrometry," Analytical Chemistry, Feb. 2001, vol. 73, No. 3, pp. 612-619.
Shenar et al. "Comparison of inert supports in laser desorption/ionization mass spectrometry of peptides: pencil lead, porous silica gel, DIOS-chip and NALDI™ target, Rapid Communications in Mass Spectrometry," 2009, vol. 23, pp. 2371-2379.

(56) References Cited

OTHER PUBLICATIONS

Takagi et al. "Preparation of monosized micro-particles of semiconductor materials," Database Inspec, The Institution of Electrical Engineers, 2004, Database Accession No. 8555685, 1 page.

Theaker et al. "Doped hydrophobic silica nano- and micro-particles as novel agents for developing latent fingerprints," Forensic Science International, 2008, vol. 174, pp. 26-34.

Tutashkonko et al. "Mesoporous Germanium formed by bipolar electrochemical etching," Electrochimica Acta, 2013, vol. 88, pp. 256-262.

Wang et al. "Biomimic Light Trapping Silicon Nanowire Arrays for Laser Desorption/Ionization of Peptides," The Journal of Physical Chemistry C, 2012, vol. 116, pp. 15415-15420.

Wei et al. "Electrospray sample deposition for matrix-assisted laser desorption/ionization (MALDI) and atmospheric pressure MALDI mass spectrometry with attomole detection limits, Rapid Communications in Mass Spectrometry," 2004, vol. 18, pp. 1193-1200.

Xiao et al. Impacts of Surface Morphology on Ion Desorption and Ionization in Desorption Ionization on Porous Silicon (DIOS) Mass Spectrometry, The Journal of Physical Chemistry C, 2009, vol. 113, No. 8, pp. 3076-3083.

Yao et al. "Enrichment of peptides in serum by C8-functionalized magnetic nanoparticles for direct matrix-assisted laser desorption/ionization time-of flight mass spectrometry analysis," Journal of Chromatography A, 2008, vol. 1185, pp. 93-101.

\* cited by examiner

METHODS OF DETECTING BIOLOGICAL PRINTS, FLUIDS OR ANALYTES THEREIN USING POROUS SEMICONDUCTOR SUBSTRATES

TECHNICAL FIELD

The present disclosure relates to substrates for use in forensic and drug compliance applications and the detection and/or analysis of small organic molecules by desorption/ionisation mass spectrometry.

CROSS-REFERENCE TO RELATED APPLICATIONS

The present application is a national state application under 35 U.S.C. 371 and claims the benefit of PCT Application No. PCT/AU2015/000263 having an international filing date of 5 May 2015, which designated the United States, which PCT application claimed the benefit of Australian provisional patent application no. 2014901629 titled "Analytical Substrates" and filed on 5 May 2014, the disclosures of each of which are incorporated herein by reference.

BACKGROUND

The detection of drugs or metabolites in samples taken from biological fluids, such as blood, is common in workplace, athlete and driver drug screening. Commonly used systems for detection and/or analysis of low molecular weight pharmacologically active constituents and metabolites (i.e. compounds of <1,000 m/z) include gas chromatography and liquid chromatography coupled to mass spectrometry (GC-MS, LC-MS). However, the sample preparation steps and analysis time required with these systems are time consuming and this restricts daily throughput of samples.

In contrast, matrix-assisted laser desorption/ionisation (MALDI) mass spectrometry can reach a high automated throughput. MALDI has become a preeminent technique in the analysis of relatively high molecular weight compounds such as polymers and proteins. The MALDI method typically involves co-crystallising the analyte with a matrix, which is generally a low molecular weight compound that can absorb the energy of a laser light pulse. Absorption of the laser energy causes the matrix to undergo a phase transition (along with the analyte). The analyte is then ionised and the ionised analyte can then be analysed with the mass spectrometer. Unfortunately, MALDI is not particularly suitable for analysing low molecular weight compounds because the matrix interferes with the analysis of the analyte.

More recently, there has been considerable interest in developing surface-assisted laser desorption/ionisation (SALDI) techniques for the analysis of low molecular weight compounds. Matrix-free SALDI mass spectrometry techniques that have been developed to date include desorption/ionisation on silicon (DIOS) (Thomas et al., 2000), nanostructure-initiator mass spectrometry (NIMS) (Northen et al., 2007), nano-assisted laser desorption ionisation (NALDI™) (Daniels et al., 2008).

DIOS and NIMS both use porous silicon (pSi) based substrates but differ in wafer dopant, pore size, depth and surface chemistry. DIOS substrates are macroporous with pore depths of less than 500 nm whereas NIMS substrates are mesoporous with pore depths in excess of 10 µm. Furthermore, DIOS substrates are generally functionalised with a perfluorinated silane (Trauger et al., 2004) whereas NIMS substrates are functionalised with a heavily fluorinated siloxane in 1,3-bis(heptadecafluoro-1,1,2,2-tetrahydrodecyl)tetramethyldisiloxane ($BisF_{17}$) (Northen, et al., 2007).

NALDI™ substrates are packed silicon nanowires (SiNWs) grown from gold nanoparticle-catalysed vapour liquid solid deposition. The nanostructures are 100 to 500 nm in length and 10 to 20 nm in diameter (Wyatt et al., 2010). The nanostructures are functionalised with pentafluorophenylpropyldimethylchlorosilane ($F_5PhPr$). The NALDI™ surface has a high nanostructure density (>100/$\mu m^2$), which has been shown to cause dramatic changes in performance (Go et al., 2005). NALDI™ has been used for the detection of low molecular weight compounds between 50-1500 Da.

The aforementioned matrix-free SALDI-MS techniques have been used for the analysis of a wide range of analytes including drugs, explosives, polymers, and forensic analysis.

The pSi target for DIOS can be prepared by etching silicon wafers to produce a porous substrate with a nanostructured surface. The analyte can be placed directly on the porous surface of the sample plate which is then used directly for SALDI-MS with little or no small molecule interference. The performance of the pSi in DIOS can be determined by the silicon type and the etching conditions that are used to produce the pSi.

In practice, the pSi plates used in DIOS techniques can be difficult to handle. This is largely due to their instability in air. Many of the known pSi plates that are used for DIOS absorb foreign matter once they are in contact with air and the absorbed foreign matter then interferes with the analysis of the analyte. Furthermore, the potential uses of pSi substrates for DIOS are presently limited to those in which a material to be analysed is introduced to the substrate plate whereas there is a need in some cases for smaller substrates that can be used to capture an analyte directly from a surface.

Additionally, in recent times the development of reproducible porous germanium (pGe) etching procedures has seen resurgence in the application of this semiconductor substrate (for example, as photonic crystals) due to its coupled electronic properties and quantum confinement effects. pGe substrates can be prepared via bipolar electrochemical etching (BEE) techniques using hydrofluoric acid (HF) or hydrochloric acid (HCl) as the electrolyte. In this technique, cathodisation is followed by an anodisation step that results in pore formation, and the cathodisation serves to protonate Ge—Ge bonds, subsequently creating a hydride terminated internal surface (Fang et al., 2007; Tutashkonko et al. 2013).

There is a need for improved porous semiconductor substrates for use in forensics and drug compliance applications and/or desorption/ionisation mass spectrometry applications.

SUMMARY

The present disclosure arises from the research of the present inventors into new porous semiconductor materials and methods for making those materials. This research has resulted in the development of new porous semiconductor microparticles (MPs) and substrates that can be used for the detection of fingerprints and also for the detection of analytes if present in biological fluids by laser desorption/ionisation mass spectrometry (LDI-MS). The research has also resulted in the development of new porous semiconductor substrates for use in matrix-free LDI-MS.

According to a first aspect, there is provided a method for detecting fingerprint(s) or biological fluid(s) from an individual on a surface of an object, the method comprising contacting the surface of the object suspected of containing fingerprint(s) or biological fluid(s) with porous semiconductor MPs under conditions to allow said MPs to adhere to fingerprint(s) or biological fluid(s) when present on the surface, and removing from the surface any non-adhered porous semiconductor MPs to provide a surface comprising porous semiconductor MPs adhered to the fingerprint(s) or biological fluid(s) when present.

In embodiments, the method of the first aspect further comprises analysing the porous semiconductor MPs adhered to said fingerprint(s) or biological fluid(s) by desorption/ionisation mass spectrometry to detect one or more target low molecular weight analyte(s) when present captured from the fingerprint(s) or biological fluid(s). The porous semiconductor MPs adhered to the fingerprint(s) or biological fluid(s) may be removed from the surface comprising porous semiconductor MPs adhered to the fingerprint(s) or biological fluid(s) prior to the analysing step, or the analysing step may be carried out in situ on the surface comprising porous semiconductor MPs adhered to the fingerprint(s) or biological fluid(s).

In embodiments of the first aspect, the method also comprises exposing the surface comprising porous semiconductor MPs adhered to the fingerprint(s) or biological fluid(s) to light of an excitation wavelength so that the porous semiconductor MPs emit light of a different wavelength and then imaging the porous semiconductor MPs adhered to the fingerprint(s) or biological fluid(s) on the basis of the emitted light. In an embodiment, the porous semiconductor MPs are intrinsically luminescent. In an embodiment, the porous semiconductor MPs are tagged with a fluorescent tag.

According to a second aspect, there is provided a method for detecting one or more target low molecular weight analyte(s) in a biological fluid, the method comprising contacting a biological fluid suspected of containing the target low molecular weight analyte(s) with porous semiconductor MPs under conditions to allow the MPs to capture the target low molecular weight analyte(s) when present from the biological fluid, and analysing the MPs by desorption/ionisation mass spectrometry to detect the target low molecular weight analyte(s) when present.

In embodiments, the method of the second aspect of the disclosure further comprises separating the porous semiconductor MPs from the biological fluid after the step of contacting the biological fluid with the porous semiconductor MPs.

In embodiments of the first and second aspects, the mean particle size of the porous semiconductor MPs is <50 μm. In specific embodiments of the first and second aspects, the mean particle size of the porous semiconductor MPs is from 10 to 15 μm.

In embodiments of the first and second aspects, the surface of the porous semiconductor MPs further comprises a fluorinated silane coating. The fluorinated silane coating may be formed from tridecafluoro-1,1,2,2-tetrahydrooctyldimethylchlorosilane ($F_{13}$).

According to a third aspect, there is provided a method for detecting one or more target analyte(s) in a fingerprint, the method comprising contacting a surface of a porous semiconductor substrate with at least one fingerprint from a fingerprint source under conditions to transfer at least part of the fingerprint to the surface of the porous semiconductor substrate, and analysing the substrate by desorption/ionisation mass spectrometry to detect the target analyte(s) when present.

In embodiments, the method of the third aspect further comprises identifying an individual using the fingerprint ridge structure on the surface of the porous semiconductor substrate. The step of identifying the individual may involve imaging the fingerprint or part thereof on the surface of the substrate.

According to a fourth aspect, there is provided a method for detecting one or more target analyte(s) in a biological fluid, the method comprising contacting a biological fluid suspected of containing the target analyte(s) with a porous semiconductor substrate under conditions to allow the porous semiconductor substrate to capture at least some of the target analyte(s) when present from the biological fluid, and analysing the substrate by desorption/ionisation mass spectrometry to detect the target analyte(s) when present.

In embodiments of the fourth aspect, the porous semiconductor substrate comprises a nanostructured substrate comprising a plurality of substantially aligned semiconductor nanopillars extending from the surface of the substrate.

In embodiments of the third and fourth aspects, the surface of the porous semiconductor substrate further comprises a fluorinated silane coating. The silane coating may be formed from pentafluorophenyl propyldimethylchlorosilane ($F_5PhPr$).

According to a fifth aspect, there is provided a method for making a porous semiconductor substrate for use in desorption/ionisation mass spectrometry, the method comprising coating a semiconductor surface with polystyrene nanospheres (PSNS) under conditions to form a tightly packed ordered array of nanospheres on the surface, reducing the diameter of the nanospheres to form an open, ordered array of nanospheres on the surface, coating the surface with a catalyst to form a catalyst-coated surface, removing the nanospheres from the surface to provide a catalyst-coated surface comprising an ordered array of holes in the catalyst coating, etching the coated surface with an etching agent that is catalysed by the catalyst to form an ordered array of substantially aligned semiconductor nanopillars (SiNPs) extending from the surface, and removing remaining catalyst from the surface.

According to a sixth aspect, there is provided a method for detecting one or more target analyte(s) in a biological fluid, the method comprising:
 obtaining a sample of a biological fluid suspected of containing one or more target analytes of interest;
 adding ammonium bicarbonate buffer to the sample of the biological fluid to provide a buffered sample;
 transferring an aliquot of the buffered sample to a surface of a porous semiconductor substrate and allowing the buffered sample to interact with the surface for at least about five minutes;
 then washing the surface of the substrate with an ammonium phosphate solution; and
 analysing the substrate by desorption/ionisation mass spectrometry to detect the target analyte(s) when present.

In embodiments of the sixth aspect, the method further comprises spiking the sample of the biological fluid with a solution containing specific target analytes of interest and an internal standard to give a spiked sample with a final concentration of target analytes in the range of from about 1 ng/mL to about 1000 ng/mL per target analyte and a final concentration of internal standard of about 50 ng/mL to about 150 ng/mL.

In embodiments of the sixth aspect, the target analyte is selected from the group consisting of opiates, amphetamines, benzodiazepines, and tropane alkaloids. In specific embodiments, the target analyte is selected from the group consisting of methylamphetamine, 3,4-methylenedioxy-N-methylamphetamine (MDMA), cocaine, oxycodone, methadone and flunitrazepam.

In embodiments of any one of the aspects of the disclosure, the porous semiconductor is coated with a coating layer that provides an internal calibrant.

In embodiments, the porous semiconductor is porous silicon (pSi). In embodiments, the porous semiconductor is porous germanium (pGe).

BRIEF DESCRIPTION OF FIGURES

Embodiments of the present disclosure will be discussed with reference to the accompanying drawings wherein.

DESCRIPTION OF EMBODIMENTS

Figure 1:
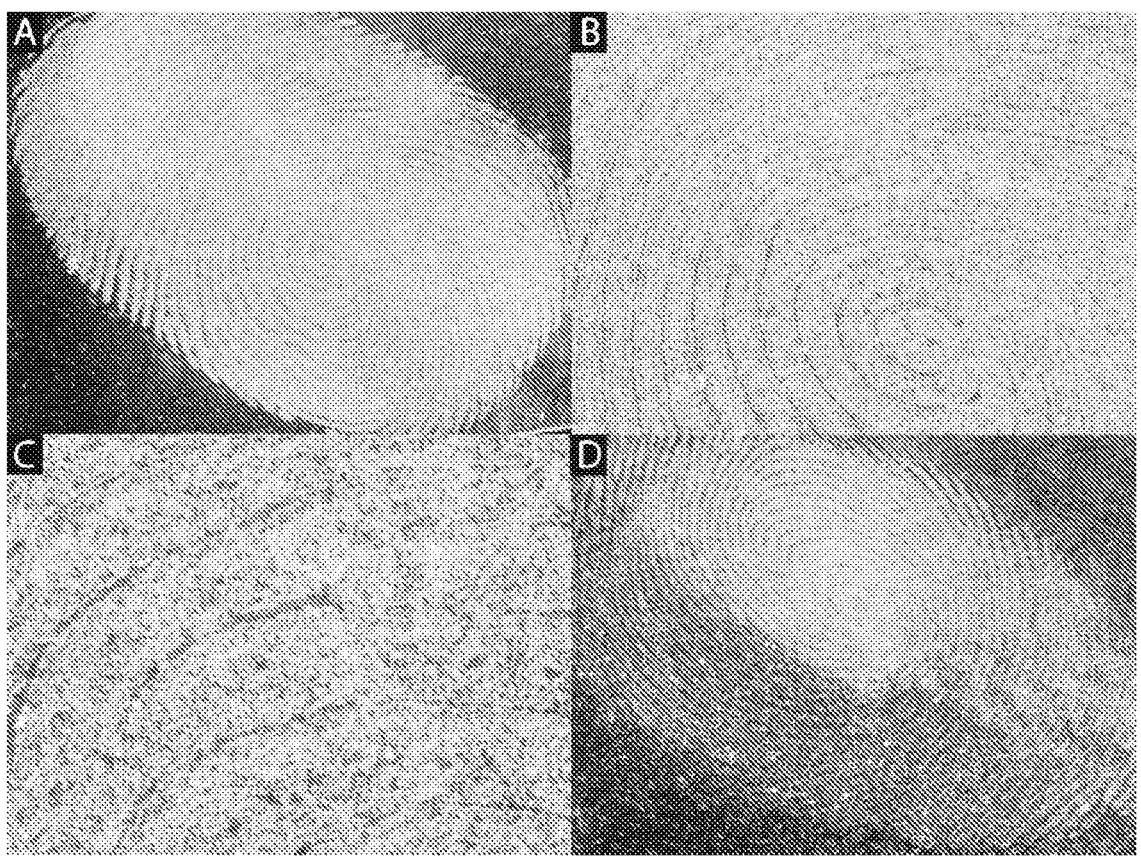
FIG. 1 shows microscope images of a fingerprint with pSi MPs that are an average 13 μm in size dusted onto a fresh latent fingerprint at (A) 1× zoom, (B) 10× zoom, and (C) 20× zoom, (D) shows a microscope image of a 9 day old fingerprint with 13 μm pSi MPs (top half of fingerprint) and 35 μm pSi MPs (bottom half of fingerprint) at 1× magnification.

The present disclosure arises from the research of present inventors into porous semiconductor substrates for use in forensic and drug compliance applications, such as fingerprinting and drug detection using surface-assisted laser desorption/ionisation mass spectrometry (SALDI-MS) and/or imaging techniques. Drug compliance and forensics are two areas of application for the materials and methods described herein but it will be appreciated that the technology can be used in a range of areas in addition to drug compliance and forensics, such as pharmacology and environmental testing.

In one aspect, provided herein is a method for detecting fingerprint(s) or biological fluid(s) from an individual on a surface, the method comprising contacting the surface suspected of containing fingerprint(s) or biological fluid(s) with porous semiconductor microparticles (MPs) under conditions to allow said MPs to adhere to fingerprint(s) or biological fluid(s) when present on the surface, and removing from the surface any non-adhered porous semiconductor MPs to provide a surface comprising porous semiconductor MPs adhered to the fingerprint(s) or biological fluid(s) when present.

Fingerprints may be left behind on a surface by the natural secretions of sweat from the eccrine glands that are present in friction ridge skin of a finger of an individual. However, it will be appreciated that in embodiment that do not utilise fingerprint identification of an individual, then the analysis as described herein could be conducted on biological or body prints or marks left on a surface from other parts of the body. Accordingly, in some embodiments described herein, the method may detect biological prints or biological marks from an individual on a surface, such as prints or marks left behind from arms, legs, buttocks, feet, face, back, chest, abdomen and the like. Biological fluids that may be left on a surface include saliva, sweat, blood, tears, urine, mucous, semen, faecal matter and the like. The biological fluids may be transferred to a surface as a result of direct contact between an individual and the surface, or the biological fluid may be transferred to the surface by non-contact means, such as when the biological fluid drips onto a surface.

The porous semiconductor microparticles particles can be "dusted" on to a surface using standard techniques. The fingerprints or biological fluid(s) may be on the original surface onto which they were transferred or they may be transferred onto another surface, such as when a fingerprint is "lifted" from a surface using adhesive tape or similar. The fingerprint may be a whole print or a partial print.

The porous semiconductor microparticles may be formed from any suitable porous semiconductor. In an embodiment, the porous semiconductor microparticles are formed from porous silicon (pSi).

A porous semiconductor substrate can be formed by conventional methods such as electrochemical wet etching which involves exposing the semiconductor to a wet solution and passing a current through a contact to the etching sample and through the solution. Alternatively, the porous semiconductor substrate can be formed by any of the methods described herein. The semiconductor substrate may be a continuous single crystal or a single crystal wafer, or polycrystalline formed semiconductor. It will be appreciated that the porous semiconductor MPs have a porous surface which has a greater surface area than an equivalent semiconductor microparticle which is non-porous. The greater surface area of the particles provides a greater contact area when the MPs are in contact with a fingerprint or biological fluid and this assists in the transfer of substances from the fingerprint or biological fluid to the particle.

The porous semiconductor has a higher absorption cross-section in the UV region, thereby allowing UV laser energy to heat the particles and desorb/ionise molecules adsorbed. In embodiments, the porous semiconductor pSi MPs described used herein have a surface area of 200-800 $m^2/g$.

The porous semiconductor MPs may be formed by comminution of a porous semiconductor substrate. The MPs can be comminuted using a suitable technique, such as sonicating, milling or grinding. The comminuted particles can then be sieved using a sieve or mesh of the desired size to provide porous semiconductor MPs suitable for the uses described herein.

The mean particle size of the porous semiconductor MPs may be <50 μm. In embodiments, the mean particle size of the porous semiconductor MPs is <50 μm, <45 μm, <40 μm, <35 μm, <30 μm, <25 μm, <20 μm or <15 μm. The mean particle size of the porous semiconductor MPs may be from 1 to 40 μm, from 1 to 20 μm, from 10 to 20 μm, from 10 to 15 μm, from 20 to 30 μm, from 30 to 40 μm, or from 40 to 50 µm. In some specific embodiments, the mean particle size of the porous semiconductor MPs is about 13.5 µm. In other specific embodiments, the mean particle size of the porous semiconductor MPs is about 35 µm.

Fingerprints contain naturally occurring compounds from the body as well as exogenous compounds, such as drugs of abuse or explosive residues, which may be left on the latent fingerprint as a result of contact with the material or may be in the systemic circulation of the individual. Therefore, fingerprints may be used to detect these exogenous compounds (referred to herein as "target analyte(s)"). On this basis, the method described above further comprises analysing the porous semiconductor MPs adhered to said fingerprint(s) or biological fluid(s) by desorption/ionisation mass spectrometry to detect one or more target analyte(s) when present captured from the fingerprint(s) or biological fluid (s).

The desorption/ionisation mass spectrometry techniques may include laser desorption/ionisation mass spectrometry (LDI-MS) techniques such as TOF-MS, SALDI-MS, SALDI-TOF-MS, SALDI-TOF, MALDI-MS, MALDI-TOF-TOF, etc. Other mass analysers which may be suitable for performing the methods of the present disclosure include Time of flight (TOF), Quadrupole, Quadrupole Ion Trap, Fourier tranform (FT), Linear Ion trap, Fourier Transform Ion Cyclotron Resonance (FTICR), Orbitrap, Quadrupole Time of Flight (Q-TOF). In TOF-MS, the sample ion is accelerated by a known voltage, and the time it takes a sample ion or fragment thereof to travel a known distance is measured. This data is then used to measure the mass of a sample molecule, as well as the mass of the fragments of a sample to identify that sample. Accordingly, the mass spectrometric technique that is used to detect the one or more target analyte(s) captured by the porous semiconductor MPs may be SALDI-TOF-MS. Specifically, mass spectra can be collected using a mass spectrometer equipped with a pulsed laser in reflectron positive mode. The laser attenuator offset used may depend on the target analyte(s) to be measured and the optimal offset for a specific analyte can be determined by the skilled person.

Advantageously, the desorption/ionisation mass spectrometry may be performed directly on the porous semiconductor MPs. That is, the surface of the porous semiconductor MPs may be analysed in a LDI-MS technique, such as SALDI-TOF-MS.

In an embodiment, the porous semiconductor MPs may be removed from the surface prior to the analysis step (i.e. ex situ analysis) or the analysis step may be carried out with porous semiconductor MPs adhered to the fingerprint(s) or biological fluid(s) on the surface (i.e. in situ analysis). Accordingly, the porous semiconductor MPs adhered to the fingerprint(s) or biological fluid(s) can be removed from the surface comprising porous semiconductor MPs adhered to the fingerprint(s) or biological fluid(s) prior to the analysing step. Otherwise, the analysing step may be carried out in situ on the surface comprising porous semiconductor MPs adhered to the fingerprint(s) or biological fluid(s).

The methods described herein can be used to detect analyte(s), such as metabolites produced as a result of metabolism of a substance by an individual, if present. The substance metabolised may be naturally produced by the individual's body (i.e. endogenous) or it may be a metabolite of a substance ingested or transferred into the body and subsequently metabolised by the individual's body (i.e. exogenous). Exogenous metabolites can include illegal drugs and their metabolites, prescribed drugs and their metabolites and/or compounds derived from dietary sources or breakdown products of the same. The methods described herein can also be used to detect contact residues, such as illegal drugs, explosives, and fire arm residues, if present.

Using commercially available software it is possible to form a mass spectral image of a fingerprint using the methods described herein. For example, a two-dimensional image showing concentration of an analyte of interest in different regions of a fingerprint can be formed by analysing the porous semiconductor MPs in different regions of the fingerprint by SALDI-MS and then building an forming an image showing the concentration of the target analyte(s) in the different regions.

Advantageously, the porous semiconductor MPs adhered to the fingerprint(s) or biological fluid(s) on the surface can be exposed to light of an excitation wavelength so that the porous semiconductor MPs emit light of a different wavelength and then imaging the porous semiconductor MPs adhered to the fingerprint(s) or biological fluid(s) on the basis of the emitted light. The imaging may be carried out using standard techniques, such as photography or microscopy.

In some embodiments, the porous semiconductor MPs are intrinsically luminescent. Intrinsically luminescent porous semiconductor MPs can be formed by contacting porous semiconductor substrates with a mild oxidant to activate photoluminescence prior to formation of MPs from the substrates. Borate buffer (pH 9.4) is a suitable mild oxidant. In these embodiments, the porous semiconductor MPs adhered to the fingerprint(s) or biological fluid(s) on the surface are exposed to UV light so that the porous semiconductor MPs luminesce and the luminescent porous semiconductor MPs adhered to the fingerprint(s) or biological fluid(s) can be imaged. An individual may be identified based on the fingerprint image using known fingerprint comparison techniques and software.

In other embodiments, the porous semiconductor MPs are tagged with a fluorescent tag. In these embodiments, the fluorescently tagged porous semiconductor MPs adhered to the fingerprint(s) or biological fluid(s) on the surface are exposed to an excitation wavelength of, for example, 575 nm or 490 nm so that the porous semiconductor MPs fluoresce and the fluorescent porous semiconductor MPs adhered to the fingerprint(s) or biological fluid(s) can be imaged, such as by fluorescence microscopy. An individual may be identified based on the fingerprint image using known fingerprint comparison techniques and software.

Fluorescently tagged porous semiconductor MPs can be formed by covalently bonding a fluorescent dye to the surface of the MPs. Suitable fluorescent dyes include, but are not limited to, lissamine and carboxy-5-fluorescein. However, it will be appreciated that other dyes may be suitable for the methods described herein, such as 5-iodoacetamidofluorescein, 5'hexadecanoylamino-fourescein, Rubeo, sypro Ruby, Deep purple, and the like. The surface of the porous semiconductor MPs can first be treated with a silane containing a reactive functional group capable of reacting with the fluorescent dye of interest to form a covalent bond. Depending on the fluorescent dye, the reactive functional group may be an amine or an isocyanate group. For example, the porous semiconductor MPs may be treated with 3-isocyanatopropyltriethoxysilane (ICPTES) to form ICPTES-functionalised MPs The IPTES-functionalised MPs can then be reacted with lissamine to form lissamine-functionalised porous semiconductor MPs. Alternatively, the porous semiconductor MPs may be treated with 3-(aminopropyl)triethoxysilane (APTES) to form APTES-functionalised MPs The APTES-functionalised MPs can then be reacted with carboxy-5-fluorescein to form carboxy-5-fluorescein-functionalised porous semiconductor MPs.

Also provided herein is a method for detecting one or more target analyte(s) in a biological fluid, the method comprising contacting a biological fluid suspected of containing the target analyte(s) with porous semiconductor MPs under conditions to allow the MPs to capture at least some of the target analyte(s) when present from the biological fluid, and then analysing the MPs by desorption/ionisation mass spectrometry to detect the target analyte(s) when present. In an embodiment, the target analytes(s) is a low molecular weight analyte(s).

The method may further comprise a step of separating the porous semiconductor MPs from the biological fluid after the step of contacting the biological fluid with the porous semiconductor MPs.

The biological fluid may be any biological fluid that can contain an endogenous or exogenous analyte of interest, such as an illicit drug or metabolite. Biological fluids include saliva, blood, urine, tears, sweat, mucous, semen, faecal matter and the like. In some embodiments, the biological fluids are selected from the group consisting of saliva, blood, urine, tears, or sweat, mucous, semen, and faecal matter. In some specific embodiments, the biological fluid is saliva. In other specific embodiments, the biological fluid is sweat. In other specific embodiments, the biological fluid is blood.

The porous semiconductor MPs can be contacted with the biological fluid in situ or the biological fluid can be removed from an individual before it is contacted with the porous semiconductor MPs. For in situ contact, the biological fluid can be removed from the individual's body and contacted with the porous semiconductor MPs in an in vitro setting. For example, saliva or blood can be taken from the individual's body using standard methods and placed into a vial. The biological fluid can be kept in the vial al for a period of time using standard procedures prior to contact with the porous semiconductor MPs, or the porous semiconductor MPs may be introduced into the vial immediately. Optionally, the biological fluid can be diluted or otherwise treated prior to contact with the porous semiconductor MPs. For example, the biological fluid may be diluted with a buffer solution.

After contacting the biological fluid for a period of time, the porous semiconductor MPs can be removed from the biological fluid and transferred to a substrate for analysis by desorption/ionisation mass spectrometry techniques such as TOF-MS, SALDI-MS, SALDI-TOF-MS, SALDI-TOF, etc as mentioned elsewhere herein. In TOF-MS, the sample ion is accelerated by a known voltage, and the time it takes a sample ion or fragment thereof to travel a known distance is measured. This data is then used to measure the mass of a sample molecule, as well as the mass of the fragments of a sample to identify that sample.

To remove the porous semiconductor MPs from the biological fluid, the mixture of porous semiconductor MPs and fluid can be centrifuged and the settled MPs removed using a pipette or the like. Alternatively, the MPs can be removed from the fluid by filtration.

One application for the methods described herein is for the detection, if present, of illicit drugs at the roadside. Some countries currently test for a range of illicit drugs including amphetamines and tetrahydrocannibinol at the roadside. In the present case, the porous semiconductor MPs can be contacted with oral fluid and then analysed by SALDI-TOF-MS in a procedure that allows for non-invasive screening of drugs.

Optionally, the porous semiconductor MPs used herein further comprise a fluorinated silane coating. Suitable fluorinated silanes include tridecafluoro-1,1,2,2-tetrahydrooctyldimethylchlorosilane ($F_{13}$). The silane coated porous semiconductor MPs can be formed by treating the porous semiconductor MPs with an oxidant to oxidise the surface of the MPs and then treating the oxidised porous semiconductor MPs with a perflourinated chlorosilane to form fluorinated silane coated porous semiconductor MPs. The oxidant may be ozone. Fluorinated silane coated porous semiconductor MPs may be more storage stable than their non-coated equivalents.

Also provided herein is a method for detecting one or more target analyte(s) in a fingerprint, the method comprising contacting a surface of a porous semiconductor substrate with at least one fingerprint from a fingerprint source under conditions to transfer at least part of the fingerprint to the surface of the porous semiconductor substrate, and analysing the substrate by desorption/ionisation mass spectrometry to detect the target analyte(s) when present. Optionally, the fingerprint on the surface of the porous semiconductor substrate can be imaged and this provides a powerful technique for detecting drugs of abuse, explosive residues or other target analyte(s) which may be left on the latent fingerprint as well as identifying an individual using the fingerprint ridge structure on the surface of the porous semiconductor substrate.

The porous semiconductor substrate may be chosen from any suitable porous semiconductor substrate. In an embodiment, the porous semiconductor substrate is a porous silicon (pSi) substrate. In an embodiment, the porous semiconductor is a porous germanium (pGe) substrate.

A pSi substrate can be formed by light-assisted anodic etching of suitable monocrystalline wafers. The etched pSi substrate can then be oxidised to form an oxidised pSi substrate. Preferably, the oxidised pSi substrate is subjected to a second pore broadening etch process that is carried out on the oxidised pSi substrate to form the pSi substrate.

A pGe substrate can be prepared using any techniques known to those skilled in the art, including via bipolar electrochemical etching (BEE) techniques using HF or HCl as the electrolyte. Cathodisation may be followed by an anodisation step that results in pore formation, and the cathodisation can protonate Ge—Ge bonds, subsequently creating a hydride terminated internal surface (Fang et al., 2007; Tutastikonko et al. 2013). In an embodiment, pGe can optionally be silanised using techniques known to those skilled in the art. However, oxidised pGe substrates are hydrophobic owing to the hydroxyl monolayer on Ge compared with the hydrated oxide present for pSi. Accordingly, in an embodiment, pGe is used as a porous semiconductor substrate without silanisation.

In embodiments, the porous semiconductor substrate further comprises a fluorinated silane coating. Suitable fluorinated silanes for forming the silane coating include pentafluorophenylpropyldimethylchlorosilane ($F_5PhPr$). The silane coated porous semiconductor substrate can be formed by treating the porous semiconductor substrate with an oxidant to oxidise the surface and then treating the oxidised porous semiconductor MPs with a perflourinated chlorosilane to form a fluorinated silane surface on the porous semiconductor substrate. The oxidant may be ozone.

Fingerprints, or parts thereof, can be transferred to the surface of the porous semiconductor substrate by contacting the finger of an individual with the surface of the porous semiconductor substrate. Alternatively, latent fingerprints may be lifted from a surface using tape and then the tape containing the fingerprint can be contacted with the surface of the porous semiconductor substrate to transfer the fingerprint or part thereof to the surface of the substrate. Alternatively still, in some instances it may be also be possible to contact the surface of the porous semiconductor substrate with another surface suspected of containing a fingerprint to thereby transfer the fingerprint or part thereof to the surface of the porous semiconductor substrate.

Drugs of abuse, explosive residues or other target analyte(s) can be detected in the fingerprint on the surface using SALDI-TOF-MS, as described previously. Advantageously, mass spectral imaging can also be used to generate an image of the fingerprint. This can then be used to identify an individual using known fingerprint matching techniques and software. Thus, a MALDI-TOF-TOF mass spectrometer can be used to perform mass imaging analysis. Appropriate imaging software can then be used to extract ion intensity map images, after processing the datasets by baseline subtraction, normalisation and data reduction.

Also provided herein is a method for detecting one or more target analyte(s) in a biological fluid, the method comprising contacting a biological fluid suspected of containing the target analyte(s) with a porous semiconductor substrate under conditions to allow the porous semiconductor substrate to capture at least some of the target analyte(s) when present from the biological fluid, and analysing the substrate by desorption/ionisation mass spectrometry to detect the target analyte(s) when present.

In embodiments, pSi substrate is a nanostructured silicon substrate comprising a plurality of substantially aligned silicon nanopillars (SiNPs) extending from the surface of the substrate. The nanostructured silicon substrate can be fabricated by coating a silicon surface with polystyrene nanospheres (PSNS) under conditions to form a tightly packed ordered array of nanospheres on the surface. The diameter of the nanospheres may then be reduced to form an open, ordered array of nanospheres on the surface. Then, the surface may be coated with a catalyst to form a catalyst-coated surface and the nanospheres are removed from the surface to provide a catalyst-coated surface comprising an ordered array of pores in the catalyst coating. The coated surface may be then etched with an etching agent that is catalysed by the catalyst to form an ordered array of vertically aligned SiNPs extending from the surface. Any remaining catalyst may be removed from the surface to provide the SiNP substrate comprising a plurality of substantially aligned SiNPs extending from a surface of the substrate.

The silicon surface may be a surface of a flat silicon wafer. The surface of the wafer may be cleaned prior to coating with PSNS. A solution of PSNS can be deposited on the surface and then spin-coated to form a self-assembled, hexagonally arranged monolayer of PSNS. In embodiments, the PSNS have a diameter of about 500 nm.

The substrate coated with PSNS can then be treated with oxygen plasma for a period of time that is sufficient to reduce the diameter of the PSNS by 20 nm to 100 nm, such as by 50 nm. This results in the formation of a gap between the PSNS. Preferably, the gap between the PSNS is less than about 300 nm, more preferably from about 70 to about 120 nm, and is most preferably about 100 nm.

The surface may be then coated with a catalyst to form a catalyst-coated surface. The catalyst may be silver (Ag) metal. The catalyst-coated surface may be formed by sputter-coating. The PSNS can then be removed from the surface by sonication water to leave a catalyst layer comprising hexagonally arranged pores where the PSNS were originally located.

The coated surface can then be etched with an etching agent using a metal-assisted chemical etching (MACE) process (Huang et al., 2011). The etching agent may be an aqueous HF/hydrogen peroxide ($H_2O_2$) solution. The degree of porosity in the SiNPs can be controlled in the etching process by varying the concentration of $H_2O_2$ whilst the concentration of HF remains constant (Chiappini et al., 2010) and/or varying the duration of the etching reaction, with longer durations resulting in an increase in the nanopillar length. For example, using etching times of 1, 5 or 20 minutes and a $H_2O_2$ concentration of 0.1 M results in nanopillar lengths of 450, 1360, and 3500 nm, respectively.

After etching, the catalyst can be removed from the surface using a strong acid such as nitric acid to provide the nanostructured substrate comprising a plurality of substantially aligned SiNPs extending from a surface of the substrate.

In an embodiment, the surface of the nanostructured semiconductor substrate further comprises a fluorinated silane coating. For example, the silane coating may be formed from pentafluorophenyl propyldimethylchlorosilane (F5PhPr).

As described, the nanostructured silicon substrate comprising a plurality of substantially aligned SiNPs extending from a surface of the substrate can be used in the detection of one or more target analyte(s) from the biological fluid by LDI-MS. The target analyte(s) can be endogenous or exogenous metabolites, illegal drugs and their metabolites or prescribed drugs and their metabolites.

The biological fluid can be deposited directly onto the SiNP substrate comprising a plurality of substantially aligned SiNPs and allowed to dry. SALDI-TOF mass spectra can then be recorded using standard techniques.

The methods described herein provide a matrix-free analytical method that allows a sample to be place directly onto a surface and analysed. This simplifies sample preparation because the analyte does not need to be mixed with a matrix or co-crystallised to produce an adequate signal.

The present inventors have also developed a novel rinsing method for contacting biological fluids suspected of containing one or more target analyte(s) with a porous semiconductor substrate. The method comprises obtaining a sample of a biological fluid suspected of containing one or more target analyte(s) of interest. Ammonium bicarbonate buffer is then added to the sample of the biological fluid to provide a buffered sample. An aliquot of the buffered sample is transferred to a surface of a porous semiconductor substrate and allowed to interact with the surface for at least about five minutes. The surface of the substrate is then washed with an ammonium phosphate solution and the substrate analysed by desorption/ionisation mass spectrometry to detect the target analyte(s) when present.

The method is suitable for detecting target analytes including opiates, amphetamines, benzodiazepines, and tropane alkaloids. Specific target analytes that can be detected using this method are methylamphetamine, 3,4-methylene-dioxy-N-methylamphetamine (MDMA), cocaine, oxycodone, methadone, and flunitrazepam.

The method may comprise spiking the sample of the biological fluid with a solution containing specific target analytes of interest and an internal standard to give a spiked sample with a final concentration of target analytes in the range of from about 1 ng/mL to about 1000 ng/mL per target analyte and a final concentration of internal standard of about 50 ng/mL to about 150 ng/mL.

Additionally, the present inventors have realised that the coating of a semi-conductor substrate can be used as an internal calibrant for high mass accuracy imaging mass spectrometry of target analytes. Accordingly, in an embodiment, the porous semiconductor is coated with a coating layer that provides an internal calibrant for desorption/ionisation mass spectrometry. For example, a semi-conductor substrate, such as a DIOS chip, can be sputter-coated with a layer of a suitable coating compound such as silver, gold, copper or platinum of the like of a known, substantially consistent thickness (eg within 0.1-1.0 nm thick, 0.1-0.5 nm thick, or 0.1-0.2 nm thick) wherein the thickness falls within the range of, for example, from between about 0.01 to 50 nm thick, 0.1 to 10.0 nm thick, 0.4 to 10 nm thick, or 0.4 to 3.4 nm thick. In embodiments, the layers of the coating compound might be about 0.4, 0.7, 1.7 or 3.4 nm thick; however, it will be appreciated that other thicknesses of the coating compound may be suitable, providing the coating can act as an internal calibrator of LDI-MS. The characteristics of the coating compound can be used to provide an internal calibrant. For example, when the coating layer is Ag, Ag clusters can be used used as internal calibrants. In an embodiment, 10 Ag clusters are used as an internal calibrant, wherein the mass of different Ag clusters are used for calibration. However, it will be appreciated that other compounds and numbers of clusters can be used to provide an internal calibrant. In an embodiment, fingermarks or biological fluids may be deposited and imaged on these coated semi-conductor substrates and an increase in mass accuracy can be demonstrated in the low mass range following internal recalibration. This method of internal calibration may provide for high mass accuracy SALDI-TOF/TOF MS of small molecules in both single measurement and mass spectrometry imaging formats.

EXAMPLES

Example 1—Formation of pSi MPs

Porous silicon (pSi) chips were prepared electrochemically using low resistivity (<0.001 Ωcm) p-type silicon wafers (siegert wafer, Germany) in an electrolyte mixture of aqueous HF (48%) and pure ethanol (in a volume ratio 3:1) for 4 min with a current density of 222 mA/cm$^2$. The pSi film was detached from the silicon substrate by the application of a constant current of 1000 mA/cm$^2$ for 20 s. The film was placed into a vial containing ethanol and subjected to ultrasonication for 20 min. The resulting pSi microparticles (MP)s were sieved using molecular sieves and a custom made sieve shaker. The particles were rinsed through the sieves with ethanol and then placed in a furnace at 100° C. for 3 h to provide pSi MPs.

Example 2—Fingerprint Detection Using pSi MPs

Size and morphology is a factor that governs the effectiveness of dusting powders to adhere to fingerprint residues. The literature suggests that the most effective dusting powders are 1-10 μm in size (Saferstein, 2004). As a result, pSi MPs that were >53 μm were not used for fingerprint dusting. FIG. 1A-C displays 13.5 μm pSi MPs dusted on freshly deposited fingerprints at different magnifications. Good fingerprint specificity was observed and clear fingerprint regions are visible. FIG. 1D displays a 9 day old fingerprint that was dusted with 13.5 (top) and 40 μm (bottom) pSi MPs, respectively. Although each of the sieved pSi MPs adhered well to the aged fingerprint more defined ridges was observed for 13.5 μm pSi MPs. As a result the 13.5 μm pSi MPs were used for further dusting experiments.

Example 3—Formation of Fluorescently Tagged pSi MPs

Figure 2:
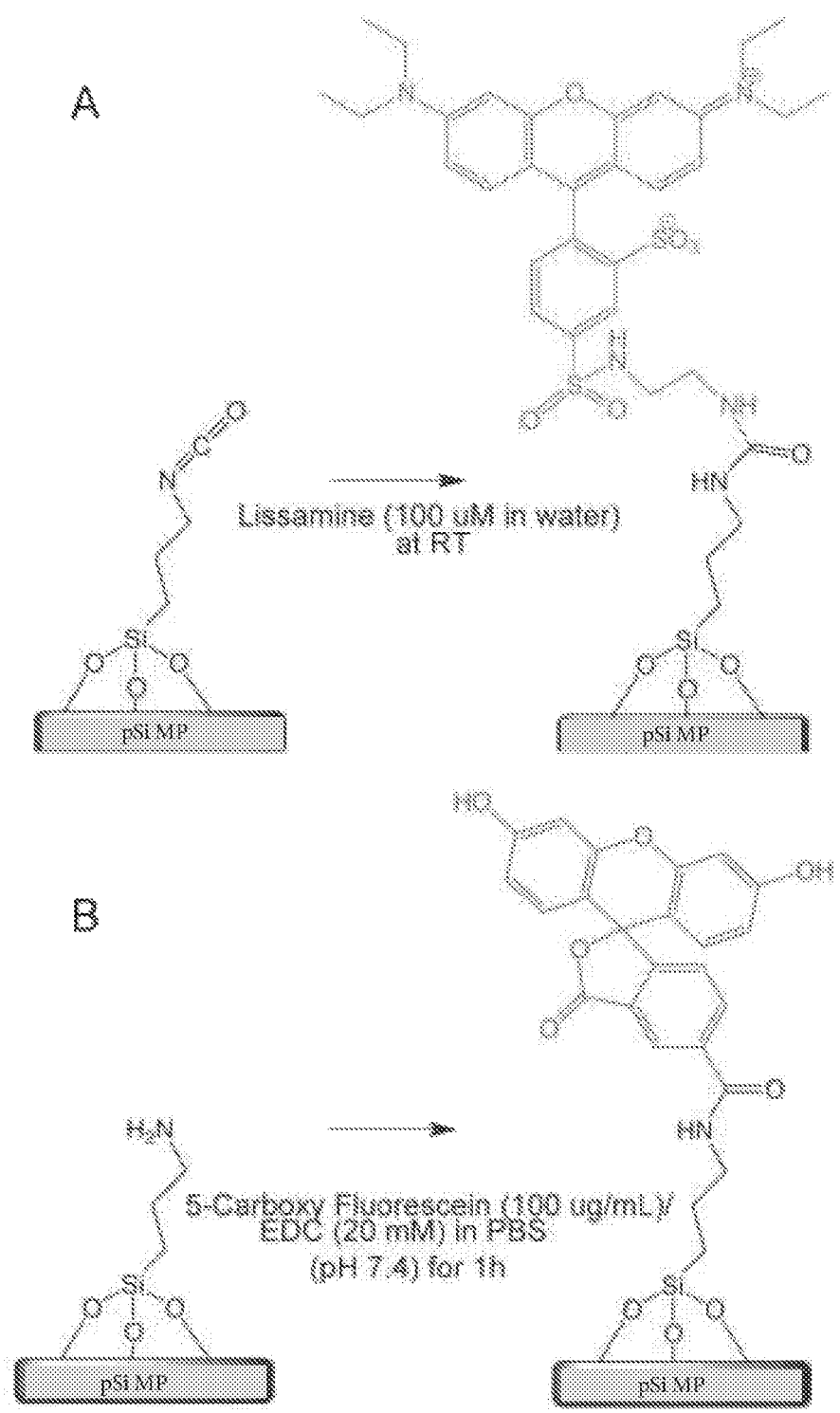
FIG. 2 shows schematically the formation of silane functionalised pSi MPs, with different fluorescent dyes attached to each silane compound, (A) conjugation of lissamine to 3-isocyanatopropyl-triethoxysilane (ICPTES)-functionalised pSi MPs and (B) conjugation of 5-carboxy fluorescein to 3-aminopropyl-triethoxysilane (APTES)-functionalised pSi MPs.

Fluorescent dyes were covalently attached to APTES- or ICPTES-functionalised pSi MPs using the chemistry depicted in FIG. 2. The pSi chips were prepared electrochemically using low resistivity (<0.001 Ωcm) p-type silicon wafers in an electrolyte mixture of aqueous HF (48%) and pure ethanol (in a volume ratio 2:1) for 4 min with a current density of 222 mA/cm$^2$. The pSi film was detached from the silicon substrate by the application of a constant current of 1000 mA/cm$^2$ for 20 s. The film was placed into a vial containing ethanol and subjected to ultrasonication for 20 min. The resulting pSi-MPs were sieved using molecular sieves and a custom-made sieve shaker. The particles were rinsed through the sieves with ethanol and then placed in a furnace at 100° C. for 3 h. Following thermal oxidation, the pSi-MPs were ozone oxidised for 1 h. After oxidation, the pSi-MPs were functionalised with APTES (50 mM) or IPTES (50 mM) in anhydrous toluene for 5 min.

Functionalisation of pSi MPs with Lissamine

Lissamine (100 ug/mL in water) was reacted with ICPTES functionalised pSi MPs for 1 h. The surface was washed 10 times with MilliQ water and then 5 times with acetone to remove any unreacted lissamine.

Functionalisation of pSi MPs with Carboxy-5-Fluorescein

Carboxy-5-fluorescein dye (100 ug/mL) and EDC (20 mM) in phosphate buffered saline (PBS, pH 7.4) were reacted with an APTES-functionalised pSi MPs for 1 h. The pSi MPs were rinsed with PBS and Milli-Q water.

Example 4—Fingerprint Detection Using Fluorescently Tagged pSi MPs

The sensitivity of the fluoroscein-conjugated pSi MPs for dusting of latent fingermarks was explored.

Figure 3:
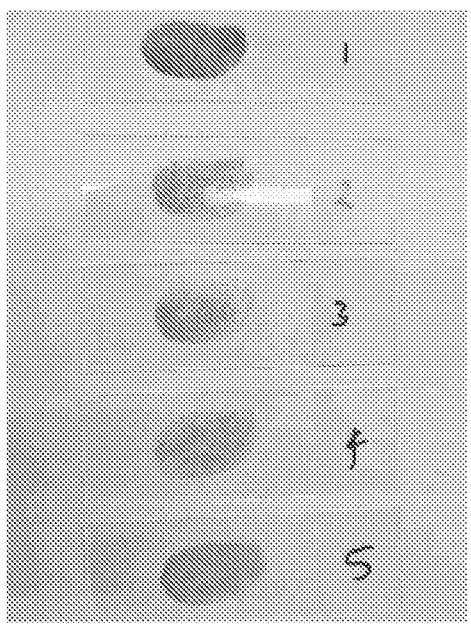
FIG. 3 shows a typical depletion series consisting of five consecutive finger depositions on glass microscope slides that have then been dusted with pSi MPs, wherein the number 1 indicates the first deposition, the number 2 indicates the second deposition, the number 3 indicates the third deposition, the number 4 indicates the fourth deposition, and the number 5 indicates the fifth deposition.

A depletion series was performed to determine the limit of adherence for the optimal pSi MPs. FIG. 3 displays a typical depletion series consisting of five consecutive finger depositions on glass microscope slides that have then been dusted with pSi MPs. After five depositions, good fingerprint specificity was still retained. This demonstrates the applicability of pSi MPs as fingerprint dusting agents.

Figure 4:
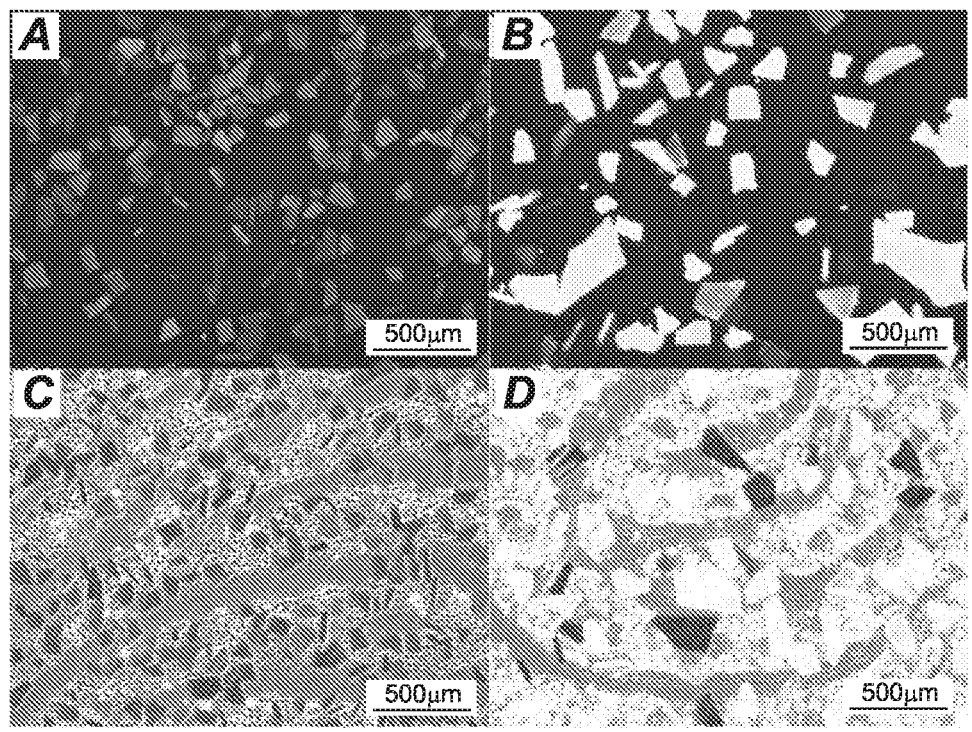
FIG. 4 shows fluorescence microscope images of (A) unsieved lissamine-conjugated ICPTES-functionalised pSi MPs, (B) unsieved 5-carboxyfluorescein-conjugated APTES-functionalised pSi MPs, and fingerprints with adsorbed (C) unsieved lissamine-conjugated ICPTES-functionalised pSi MPs and (D) unsieved 5-carboxyfluorescein-conjugated APTES-functionalised pSi MPs.

FIG. 4 shows the obtained fluorescence microscopy images for the conjugation of lissamine to ICPTES-functionalised pSi MPs (FIG. 4A) and 5-carboxy fluorescein to APTES-functionalised pSi MPs (FIG. 4B) adhering to fingerprint residues. Here, particles were not sieved or size selected. The fluorescence microscopy images overlaid with brightfield microscopy images show that the pSi MPs are confined nicely to the fingerprint regions and fluoresce well (FIG. 4C-D).

Figure 5:
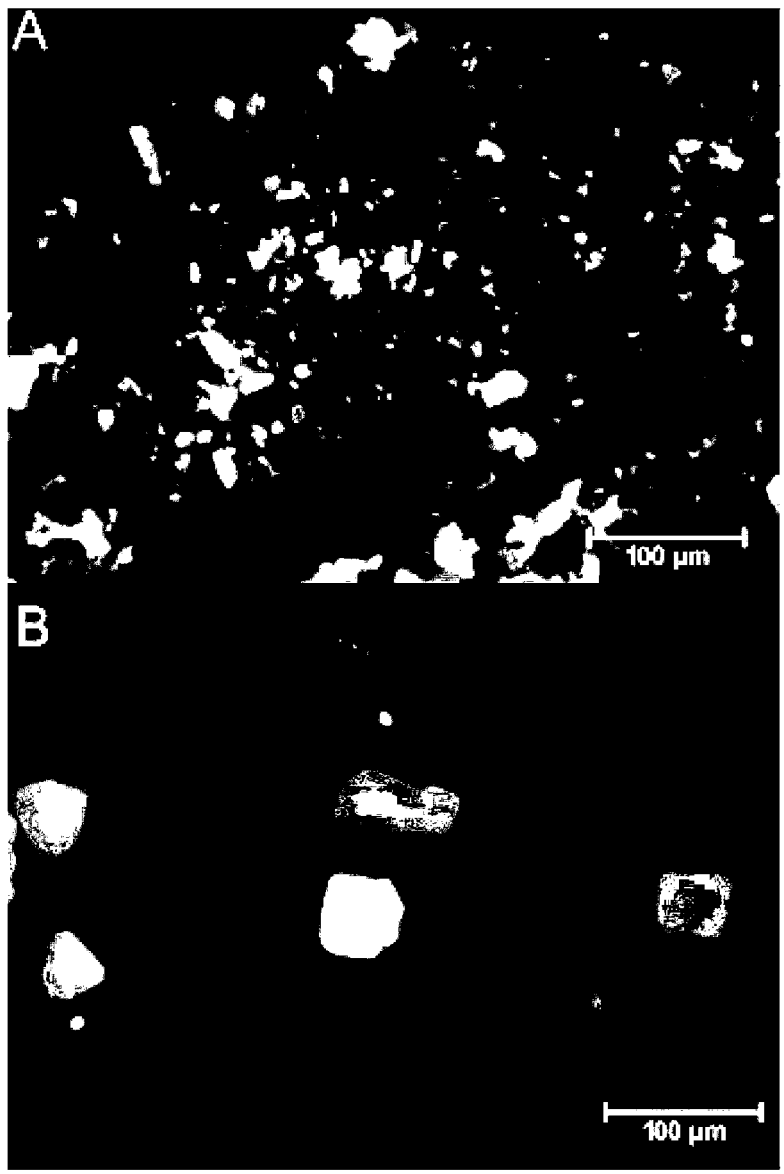
FIG. 5 shows fluorescence microscopy images of 5-carboxyfluorescein-immobilised APTES-functionalised pSi MPs for (A) <25 μm and (B) 25-53 μm sieved pSi MPs.

FIG. 5 shows the observed fluorescence microscopy images of sieved pSi MPs that were functionalised with 5-carboxy fluorescein.

Example 5—Formation of Photoluminescent pSi MPs

Figure 6:
FIG. 6 shows a photograph of a tube of dried luminescent pSi MPs under UV light.

Luminescent pSi MPs were prepared using an aqueous borate buffer solution (pH=9.2) (FIG. 6). The pSi chips were prepared electrochemically using low resistivity (<0.001

Ωcm) p-type silicon wafers in an electrolyte mixture of aqueous HF (48%) and pure ethanol (in a volume ratio 2:1) for 4 min with a current density of 222 mA/cm$^2$. The pSi film was detached from the silicon substrate by the application of a constant current of 1000 mA/cm$^2$ for 20 s. Subsequently, the pSi MP film was immersed into a borate buffer (pH 9.4) for 10 min and then rinsed with copious amounts of water. The pSi film was fractured into pSi MPs via ultrasonication for 20 min. The resulting photoluminescent pSi MPs were ozone oxidised and dried under vacuum until required for use.

Example 6—Fingerprint Detection Using Photoluminescent pSi MPs

Figure 7:
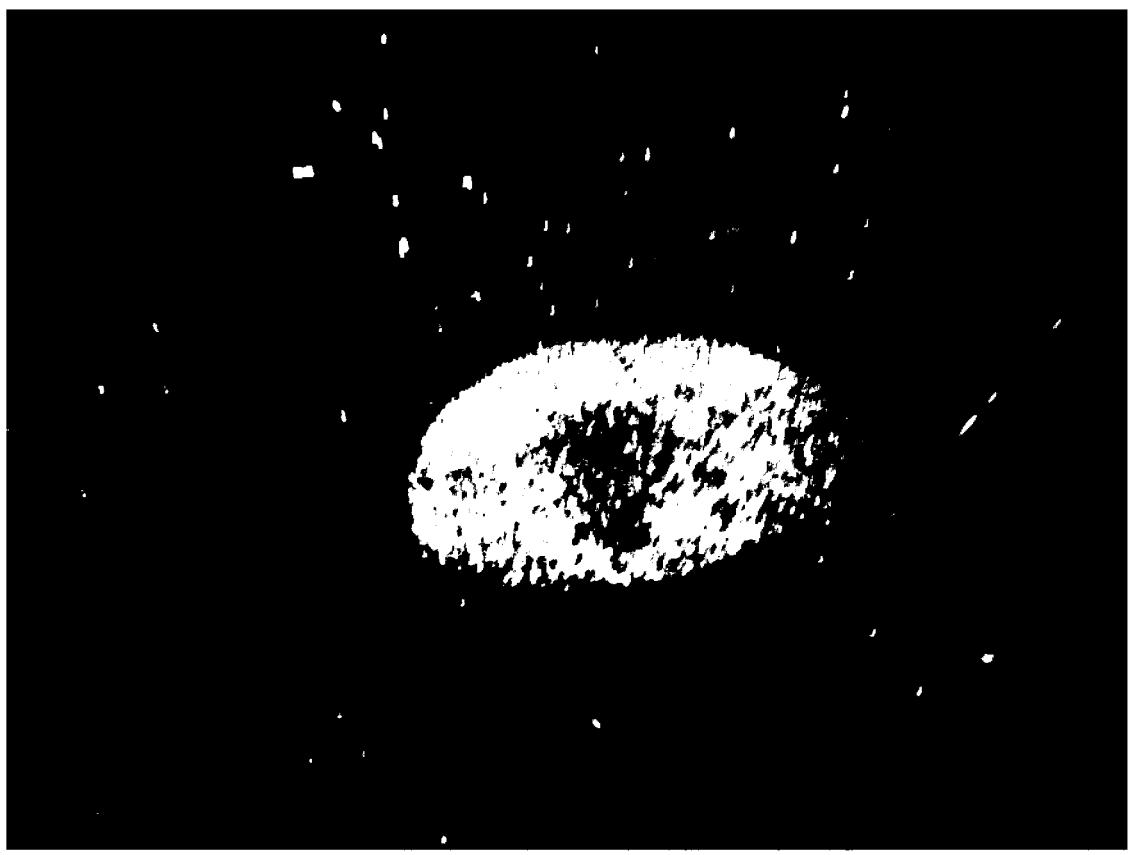
FIG. 7 shows a photograph of a fingerprint dusted with luminescent pSi MPs and excited under UV light.

Intrinsically luminescent pSi MPs offer an alternative fluorophore that can be as photostable as conventional II-IV quantum dots (Gu et al., 2010). FIG. 6 shows a photograph of luminescent pSi MPs under UV light and FIG. 7 shows a fingerprint dusted with luminescent pSi MPs and excited under UV light.

Example 7—Detection of Small Organic Molecules Using Silane-Coated pSi MPs

Figure 8:
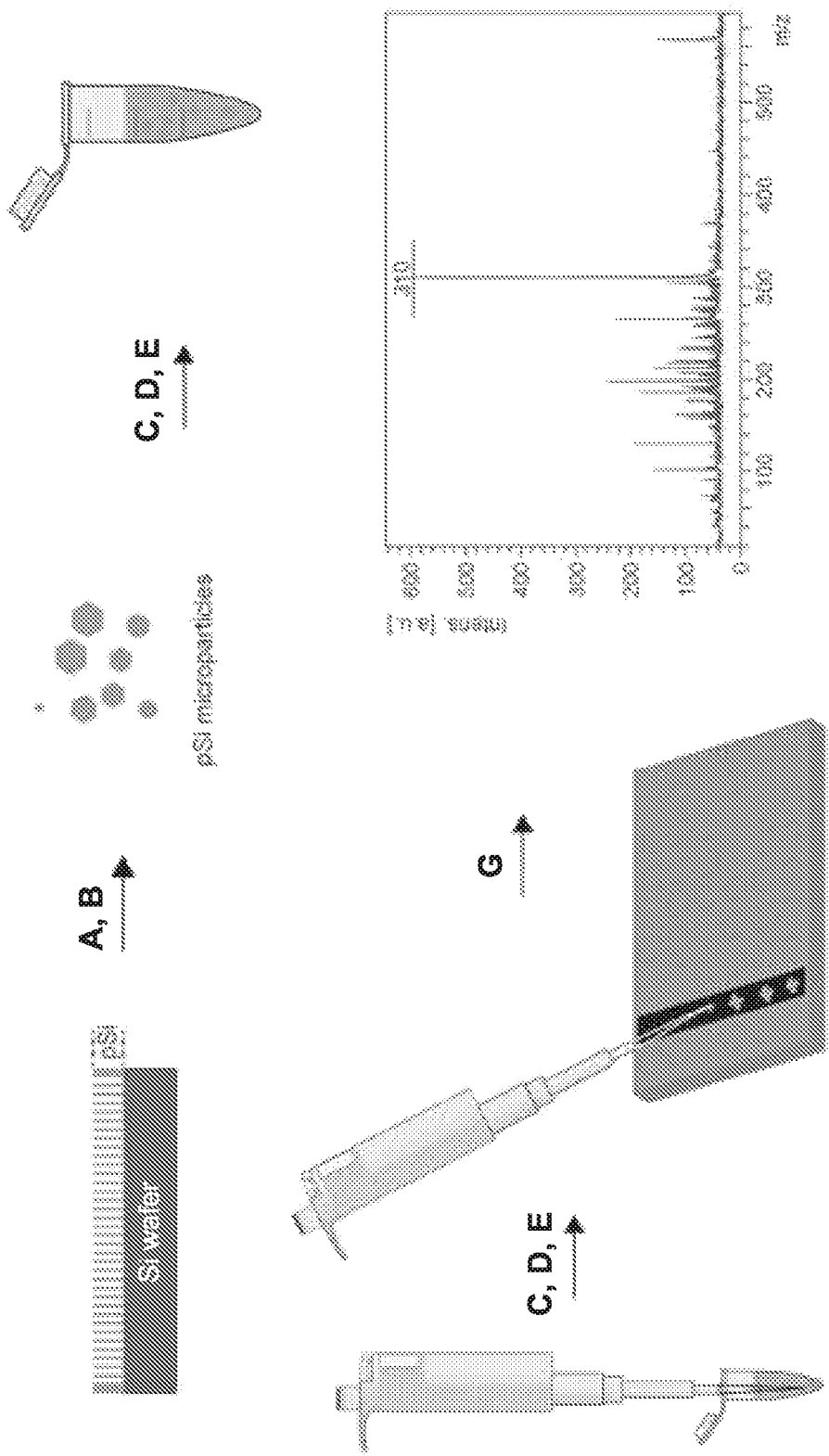
FIG. 8 shows a schematic representation showing the steps of a process for detecting one or more target low molecular weight analyte(s) in a biological fluid using pSi MPs wherein a silicon wafer undergoes (A) electropolishing and (B) sonication for 20 min to produce pSi MPs, which then undergo (C) centrifugation and drying in a furnace at 100° C., (D) ozone oxidation for 1 hr, and (E) neat silanisation with $F_{13}$ the results in MPs are then (F) pipetted onto MALDI target plate which is then (G) analysed by MALDI.

The use of pSi MPs for the detection of small organic molecules is shown schematically in FIG. 8.

Methanol (99.9%) and HF (48%) were obtained from Merck (Melbourne, VIC). Ethanol (100% undenatured) was purchased from Chem Supply (Gillman, SA). $F_{13}$ was purchased from Gelest Inc. (Morrisville, Pa.).

The pSi chips were prepared electrochemically using low resistivity (<0.001 Ωcm) p-type silicon wafers (siegert wafer, Germany) in an electrolyte mixture of aqueous HF (48%) and pure ethanol (in a volume ratio 3:1) for 4 min with a current density of 222 mA/cm$^2$. The pSi film was detached from the silicon substrate by the application of a constant current of 1000 mA/cm$^2$ for 20 s. The film was placed into a vial containing ethanol and subjected to ultrasonication for 20 min. pSi MPs were sieved immediately after sonication to obtain pSi MPs that were approximately 64 μm in size. The pSi MPs were rinsed through the sieve pans using undenatured ethanol. This rinsing process was repeated several times to achieve the desired particle size distribution. The pSi MPs were removed from the sieves and dried in an oven at 100° C. overnight. The resulting pSi MPs was oxidised at 100° C. for 3 h. Following thermal oxidation, the pSi MPs were ozone oxidised for 1 h. After oxidation, the pSi MPs were functionalised with neat $F_{13}$ at 80° C. for 2 h. The MPs were centrifuged and rinsed 10 consecutive times with ethanol. Excess ethanol was removed and the pSi MPs was dried in the oven at 80° C. for 30 min.

Stock solutions of methadone, MDMA and cocaine at 0.1 mg/mL were prepared by diluting the content of each certified standard ampoule to a final volume of 10 mL in a volumetric flask. Solutions were stored at −20° C. Working solutions at 1000 ng/mL were obtained by diluting the stock solutions with MilliQ. Working solutions were kept at +4° C. and prepared fresh every two weeks. Illicit drug solutions at varying concentrations (100-1000 ng/mL in water) were prepared from the working solutions immediately prior to analysis. Functionalised pSi MPs (2 mg) were immersed into illicit drug solutions and vortexed for 30 s. After 15 min pSi MPs were removed from the drug solution and pipetted onto double-sided carbon tape on a MALDI-TOF MSP386 steel target plate. Any residual solution was aspirated using a micropipette.

Mass spectra were collected using an Autoflex Series III Bruker MALDI-TOF-TOF mass spectrometer equipped with a SmartBeam (337 nm, Nd:YAG) 200 Hz pulsed laser, operated at 200 Hz frequency, laser attenuator offset of 12-20% in reflectron positive (RP) mode. Mass spectra were generated by averaging 500 individual laser shots. Data acquisition used flexControl 3.3 (build 85) software and data analysis was performed using flexAnalysis version 3.3. Instrumental parameters for the RP acquisition were set as follows: 19.00 and 16.80 kV for the ion source 1 and 2, respectively, 8.25 kV for the lens and 21.00 and 9.40 kV for reflector 1 and 2, respectively. Quadratic external calibration of the TOF tube was performed before each acquisition on the monoisotopic masses of α-cyano-4-hydroxycinnamic acid (CHCA) adducts, namely CHCA[M+H−H$_2$O]$^+$, CHCA[M+H]$^+$, CHCA[M+Na]$^+$, CHCA[2M+H−CO$_2$]$^+$, CHCA[2M+H]$^+$ and CHCA[3M+Na$_2$]$^+$.

Example 8—Fingerprint and Drug Detection Using Silane-Coated pSi Substrates

Figure 9:
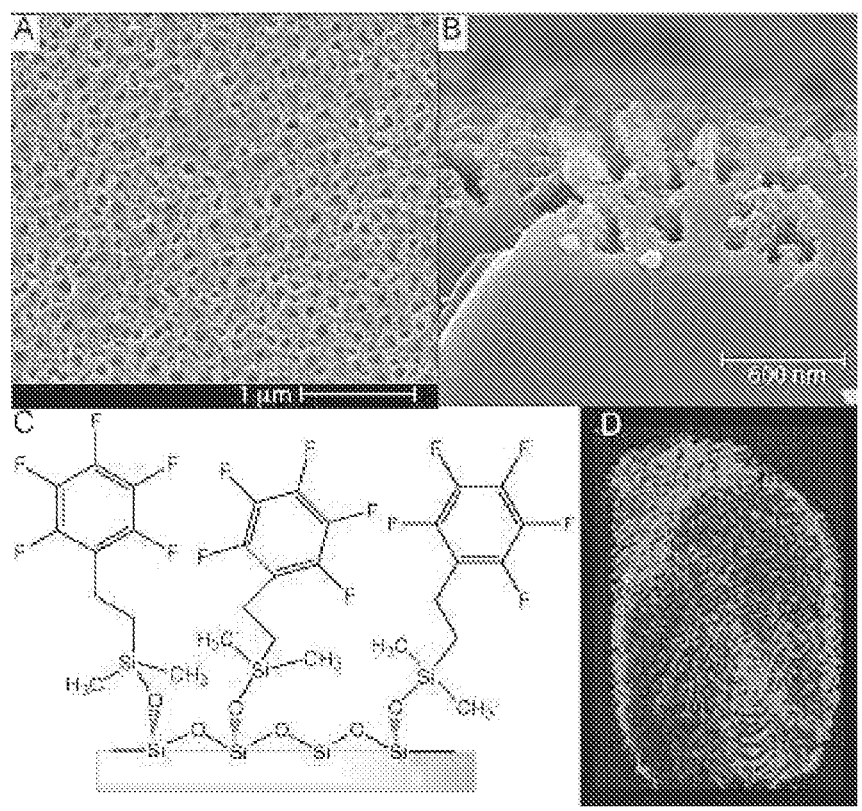
FIG. 9 shows scanning electron microscopy (SEM) micrographs of (A) DIOS substrate, and (B) cross sectional view of DIOS, and (C) pSi functionalised with pentafluorophenylpropyldimethylchlorosilane and (D) mass spectrometry imaging of fingerprint sweat.

Monocrystalline (0.008-0.02 Ωcm) antimony doped n-type Si (100) wafers from Silicon Quest International (CA, USA) were fabricated by light-assisted anodic etching at a constant current of 3.2 mA/cm$^2$ for 2 min in a 1:1 HF/ethanol electrolyte solution. The freshly-etched pSi was ozone-oxidised at a flow rate of 3.25 g/h using an Ozone-Generator 500 (Fischer, Germany). Following oxidation, the wafer was subjected to a second pore broadening etch using 5% HF/MilliQ water for 30 s. Subsequently, the double etched surface was ozone oxidised (as above) for a second time. The hydroxyl-terminated surface was then silanised via the addition of 80 μL of neat silane for 15 min at 90° C. After silanisation, the pSi arrays were washed extensively with toluene and dried under a stream of nitrogen gas and then stored under vacuum until required. FIG. 9 shows SEM images of the substrate and a schematic showing the silane functionalised substrate.

Figure 10:
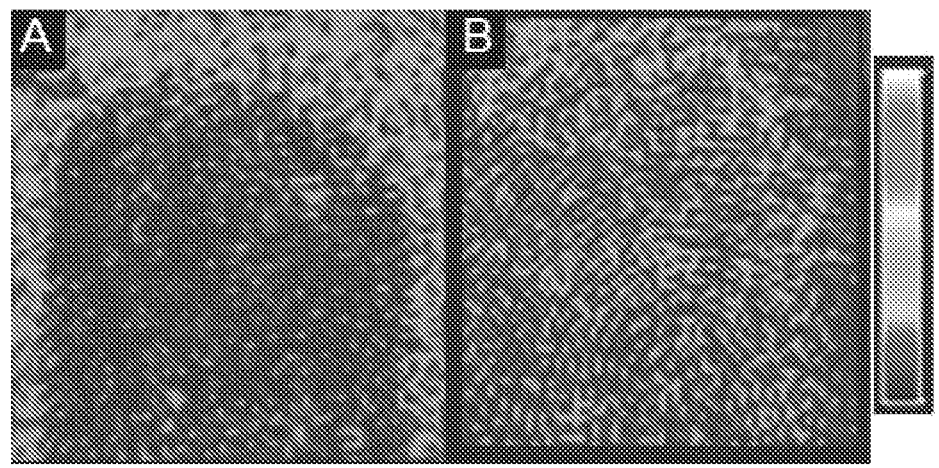
FIG. 10 shows mass spectrometry imaging of subject at (A) pre-dose and (B) t=1 hr post administration of 30 mg of codeine, the mass spectral peak of 300 m/z was selected corresponding to the m/z of codeine.

An Autoflex Series III Bruker MALDI-TOF-TOF spectrometer was used to perform mass imaging analysis in RP mode in the range 20-1200 Da with a spatial resolution of 100 μm and summing 200 laser shots for each measuring point. FlexImaging 2.1 (build 25) (Bruker-Daltonics) was used to control flexControl 3.3 during the acquisition. FlexImaging was used to extract the ion intensity map images, after processing the datasets by baseline subtraction, normalisation and data reduction. ClinProTools 2.2 (build 83) was used as spectra analysis and visualisation tool. FIG. 10 shows mass spectrometry images of fingerprints from a subject pre-dose and 1 h post administration of 30 mg of codeine. The mass spectral peak of 300 m/z was selected corresponding to the m/z of codeine.

Example 9—Preparation of pSi Substrates Having Ordered SiNPs

Figure 11:
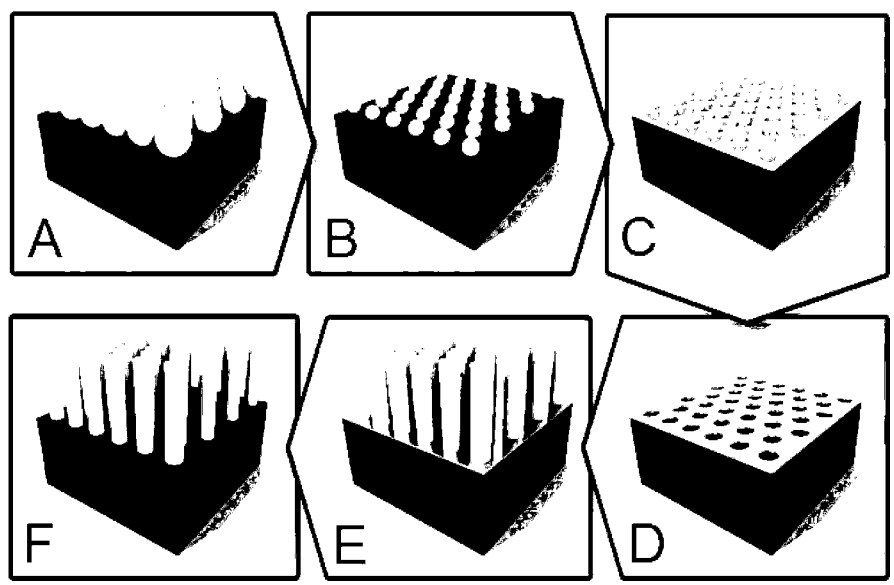
FIG. 11 shows a schematic representation of the SiNP array substrate fabrication process, with (A) spin-coating of PSNS on a Si surface, (B) treatment of the PSNS layer with $O_2$ plasma, (C) sample following silver (Ag) deposition, (D) removal of the PSNS layer, (E) etching with $HF/H_2O_2$ to produce the SiNP array substrate, and (F) SiNP array substrate after the removal of the Ag layer.

The steps of this fabrication process are shown schematically in FIG. 11.

Sulfuric acid (H$_2$SO$_4$, 95-97%) and HF (48%) were purchased from Scharlau Chemie (Chem-Supply Pty. Ltd. Australian representation). H$_2$O$_2$ (30%) was purchased from Merck (Australia). Nitric acid (70%) was purchased from Sigma-Aldrich (Australia). The polystyrene nanosphere (PSNS) solution was purchased from Polysciences (USA)

and diluted (1:1, v/v) with methanol solution containing Triton X-100 (1:400, v/v) before spin-coating. A peptide mixture consisting of angiotensin I, angiotensin II, substance P, bombesin, ACTH clip 1-17, ACTH clip 18-39 and somatostatin 28 was purchased from Bruker-Daltonics (Germany). Certified standard solutions of methadone and the internal standard methadone-d5 were kindly provided by Forensic Science South Australia (Australia).

All SEM imaging and characterisation were done using a Quanta 450 FEG Environmental SEM (FEI, Netherlands) fitted with solid state detector (SSD) and operating at 30 kV in high vacuum mode. Length measurements were performed using the SEM's operating software.

IR characterisation of the surface chemistry was carried out using a Nicolet Avatar 370 (Thermo Electron Corp.) fitted with a mercury-cadmium-telluride (MCT) detector. The collection of spectra was done using a Diffuse Reflectance Infrared Fourier Transform (DRIFT) accessory and recorded using the software OMNIC version 7.3. Scans were recorded in the range of 500-4000 $cm^{-1}$ at a resolution of 4 $cm^{-1}$. Background spectra were collected off a clean flat silicon substrate with the same type and resistivity as the silicon nanopillar (SiNP) substrates in dry air to minimise any background noise that might result from atmospheric water vapour and carbon dioxide.

Flat silicon wafers (P-type, 3-6 Ωcm, <100>, Siltronix) were cut to 2×2 $cm^2$ pieces and cleaned by sonication in 1:1 solution of ethanol:acetone for 5 min, then sonication again in MilliQ water for 5 min. This was followed by dipping the wafers into boiling piranha solution (2:1 $H_2SO_4$:$H_2O_2$ v/v, 75° C.) for 1 h to remove organic contaminants, then washed with MilliQ water and dried with $N_2$ jet.

Figure 12:
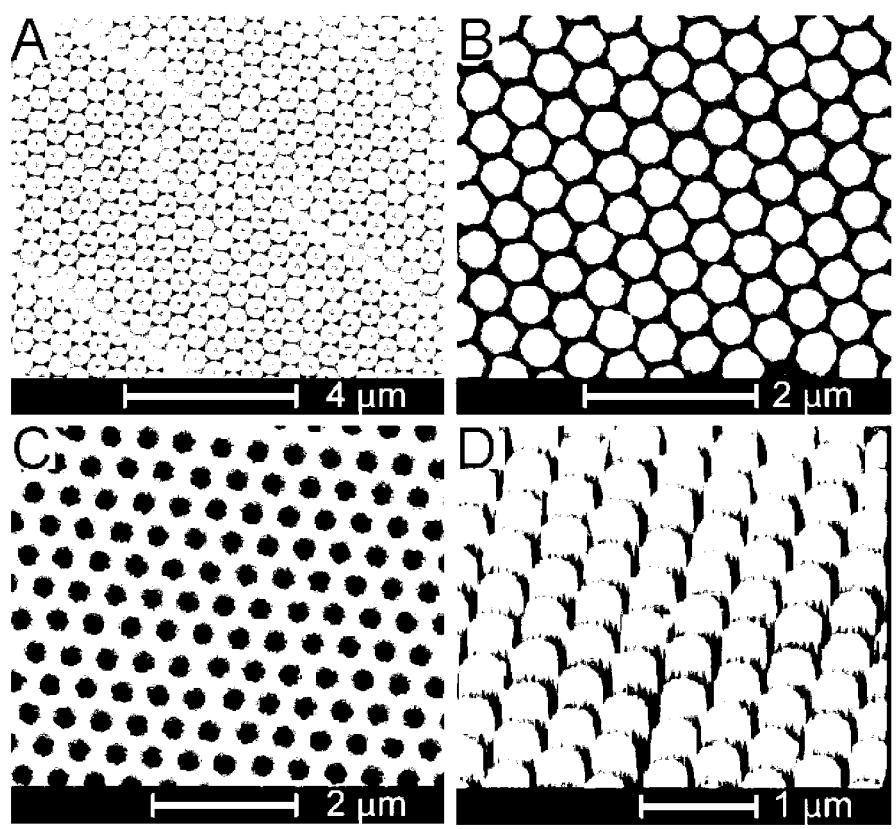
FIG. 12 shows SEM micrographs of the different stages in the SiNPs fabrication process with (A) spin-coated monolayer of PSNS after treatment in $O_2$ plasma, (B) PSNS layer after the deposition of a 40 nm Ag layer, (C) the Ag layer after removal of the PSNS layer, and (D) the SiNP array after etching in an aqueous solution of $HF/H_2O_2$.

A solution of 500 nm PSNS (50 μL) was deposited on cleaned wafers and then spin-coated (Laurell Technologies, WS-650MZ-23NPP spin-coater, USA) at 200 rpm to form a self-assembled, hexagonally arranged monolayer of PSNS. This was directly followed by a 20 s spin at 1500 rpm to remove any excess solution present around the edges of the wafer. The substrate was then etched with $O_2$ plasma using an HHV TF600 sputter-coater fitted with a PLC control system. The plasma was generated with an RF power system using 50 W and oxygen flow rate of 15 $cm^3$/min. The etching treatment was conducted for 7 min at a pressure of 2.00× $10^{-2}$ mbar. This resulted in a reduction of the diameter of the PSNS from the original size of 500 nm to 450 nm, thus creating a 100 nm wide gap between the spheres. FIG. 12A shows a representative SEM image of non close-packed arrangement of the PSNS monolayer after treatment with $O_2$ plasma.

The substrate was then sputter-coated with Ag to form a 40 nm thick Ag layer. The Ag sputter-coating was performed using an HHV TF600 sputter-coater fitted with a PLC control system. The sputter-coating was carried out using a DC power supply set at 100 W with a flow rate of Ar gas set at 10 $cm^3$ $min^{-1}$ to generate a pressure of 1.00×$10^{-2}$ mbar inside the chamber. The sputter-coating was performed for a total of 4 min to generate a 40 nm layer of Ag. FIG. 12B shows the PSNS layer after sputter-coating with a 40 nm thick Ag layer.

The PSNS were then removed from the surface by sonication in MilliQ water for 5 min followed by washing with ethanol, acetone, and MilliQ water. After removal of the PSNS, the remaining Ag layer featured hexagonally arranged holes where the PSNS were originally placed (FIG. 12C).

MACE was then carried out in a 20 mL standard Teflon container by diluting HF (48%, Scharlau) and $H_2O_2$ (30%, Merck) in MilliQ water. All etching solutions were prepared with HF concentrations of 4.8 M while $H_2O_2$ concentrations were varied from 0.1 M to 0.3 M to control the degree of porosity (Chiappini et al., 2010). The Teflon container was sealed and the reactions were carried out at room temperature for different durations. After this, samples were washed with MilliQ water and dipped into concentrated $HNO_3$ (70%, Sigma) for several minutes to remove the Ag layer, followed by washing with MilliQ water and acetone, and drying with a $N_2$ gas jet. A representative image of a vertical array of SiNPs formed as a result of etching the Ag-covered Si substrate in HF/$H_2O_2$ is shown in FIG. 12D. The length of the SiNPs was determined by controlling the duration of the HF/$H_2O_2$ etching.

Figure 13:
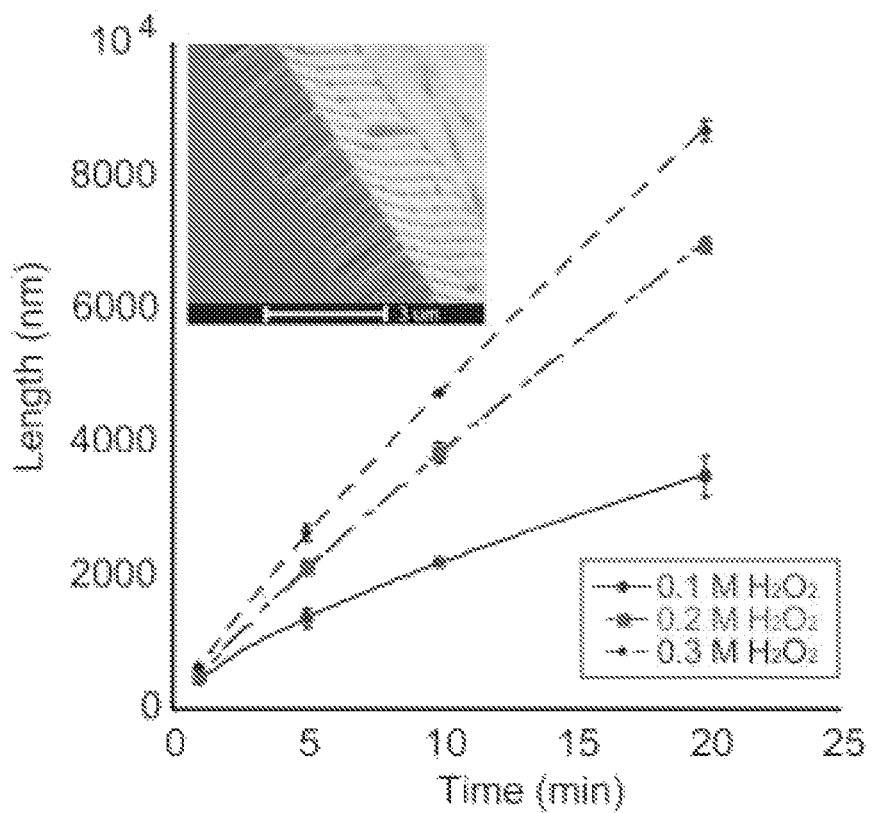
FIG. 13 shows a graph showing the length of the SiNP as a function of the duration of the $HF/H_2O_2$ etching when etching was carried out at room temperature in a solution of 4.8 M HF with $H_2O_2$ concentrations of 0.1, 0.2, and 0.3 M, inset shows a representative SEM micrograph with a cross-sectional view of a SiNP array. Scale bar is 3 μm.

A set of SiNP arrays was prepared by varying the duration of the etching reactions for each sample in the set as well as the concentration of $H_2O_2$ in the etching solution for each duration (values of 0.1 M, 0.2 M and 0.3 M were used), followed by measuring SiNP lengths using SEM imaging of cross-sections of the etched samples FIG. 13 shows a graph detailing the relationship between the mean SiNP length and the etching duration. As FIG. 13 shows, longer etching durations result in an increase in the nanopillar length. Additionally, the rate of this increase was highly dependent on the concentration of the constituents of the etching solution. From the data it was evident that increasing the concentration of the oxidising agent ($H_2O_2$) affected the rate of etching and consequently the length of the SiNP. The variation in the etching rate between the solutions with different $H_2O_2$ concentrations started out with negligible difference at lower etching times (~1 min) and became progressively more prominent as the etching duration increased. Furthermore, the etching rate of the 0.1 M $H_2O_2$ solution gradually decreased with increasing etching duration. We postulate that this is a result of diminishing supply of $H_2O_2$ molecules as the reaction progresses. At increased $H_2O_2$ concentration, the etching rate is more linear (R2 values of 0.9970 and 0.9975 for 0.2 M $H_2O_2$ and 0.3 M $H_2O_2$ solutions, respectively).

Figure 14:
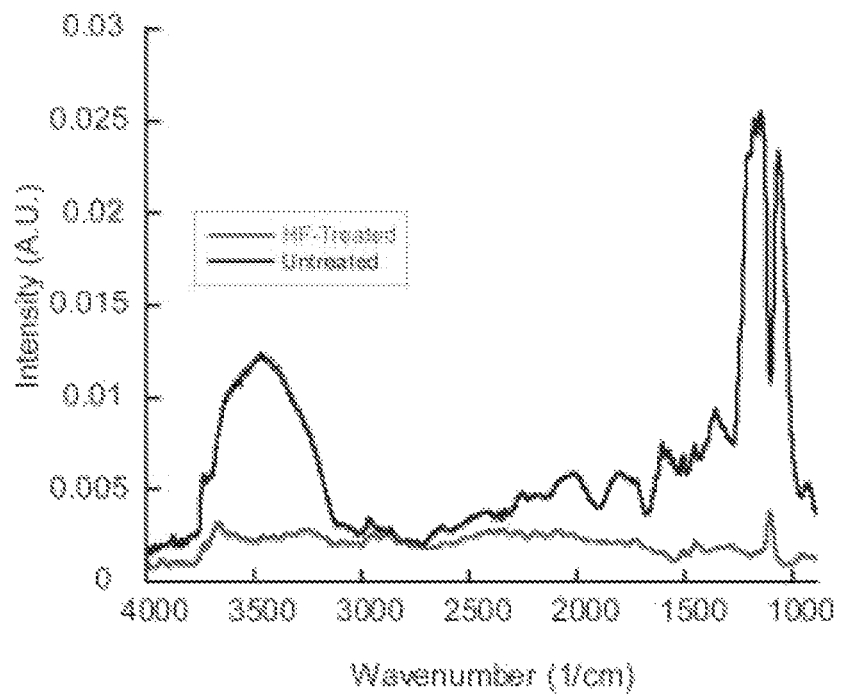
FIG. 14 shows FTIR spectra collected using Diffuse Reflectance Infrared Fourier Transform on two SiNP arrays, where the untreated SiNP array was taken after fabrication directly without any further modification while the HF-treated SiNW array was dipped in 5% HF for 5 min.

IR spectroscopy was used to investigate the surface chemistry of the SiNP arrays. The SiNPs had silicon oxide groups at the time when the SALDI-TOF-MS experiments were conducted (FIG. 14).

Example 10—Detection of Peptides by SALDI-TOF-MS Using Porous SiNP Arrays

Working solutions of a peptide mixture containing angiotensin I and II, substance P, bombecin, ACTH clip 1-17, ACTH clip 18-39, and somatostatin 28 were prepared by dissolving the peptide mixture in 125 μL of 0.1% trifluoroacetate (TFA). The working solution was separated into 5 μL aliquots and stored at −20° C. Aliquots of peptide (2 μL) solutions were deposited onto the SiNP array substrates of Example 7 and allowed to completely evaporate. Upon evaporation, SiNP substrates were mounted on a modified MALDI target plate (MTP384, Bruker Daltonics, Germany) using double-sided carbon tape.

Mass spectra were collected using an Autoflex Series III Bruker MALDI-TOF mass spectrometer equipped with a SmartBeam (337 nm, Nd:YAG) 200 Hz pulsed laser, operated at 200 Hz frequency and laser attenuator offset of either 30% (for methadone analysis) or 70% (for peptides analysis) in reflectron positive mode. Mass spectra were generated by averaging 100 individual laser shots per spot, while using 5 spots per surface. This was done in order to minimise the effects of surface-to-surface variations during signal measurement. Data acquisition used flexControl 3.3 (build 85) software and data analysis was performed using flexAnalysis version 3.3. Quadratic external calibration of the TOF tube was performed on the monoisotopic masses of CHCA adducts before each analysis.

The peptides in the peptide mixture span a quasimolecular ion weight range from 1047 Da (angiotensin II) to 3147 Da (somatostatin). Three SiNP arrays were fabricated using etching times of 1 min, 5 min, and 20 min and an $H_2O_2$ concentration of 0.1 M, resulting in lengths of 450, 1360, and 3500 nm, respectively. Different SiNP diameters affected signal generation greatly. When nanopillars with 350 nm diameter and inter-nanopillar spacing of 300 nm were used, no signal generation was observed from any of the peptides. However, when the SiNP diameters were set to 450 nm and the inter-nanopillar spacing was 100 nm, signal from the peptides started to show. Therefore, the spacing between nanopillars was an important parameter, in analogy to the pores in DIOS platforms where it has been noted that the size of the pores plays an important role in whether or not signal generation can occur (Guinan et al., 2012; Ronci et al., 2012). Additionally, pore sizes in the range of 70-120 nm are commonly used for DIOS based substrates (Shen et al., 2000; Xiao et al., 2009; Northen et al., 2007). The inter-nanopillar spacing used here (100 nm) fell within that range.

Figure 15:
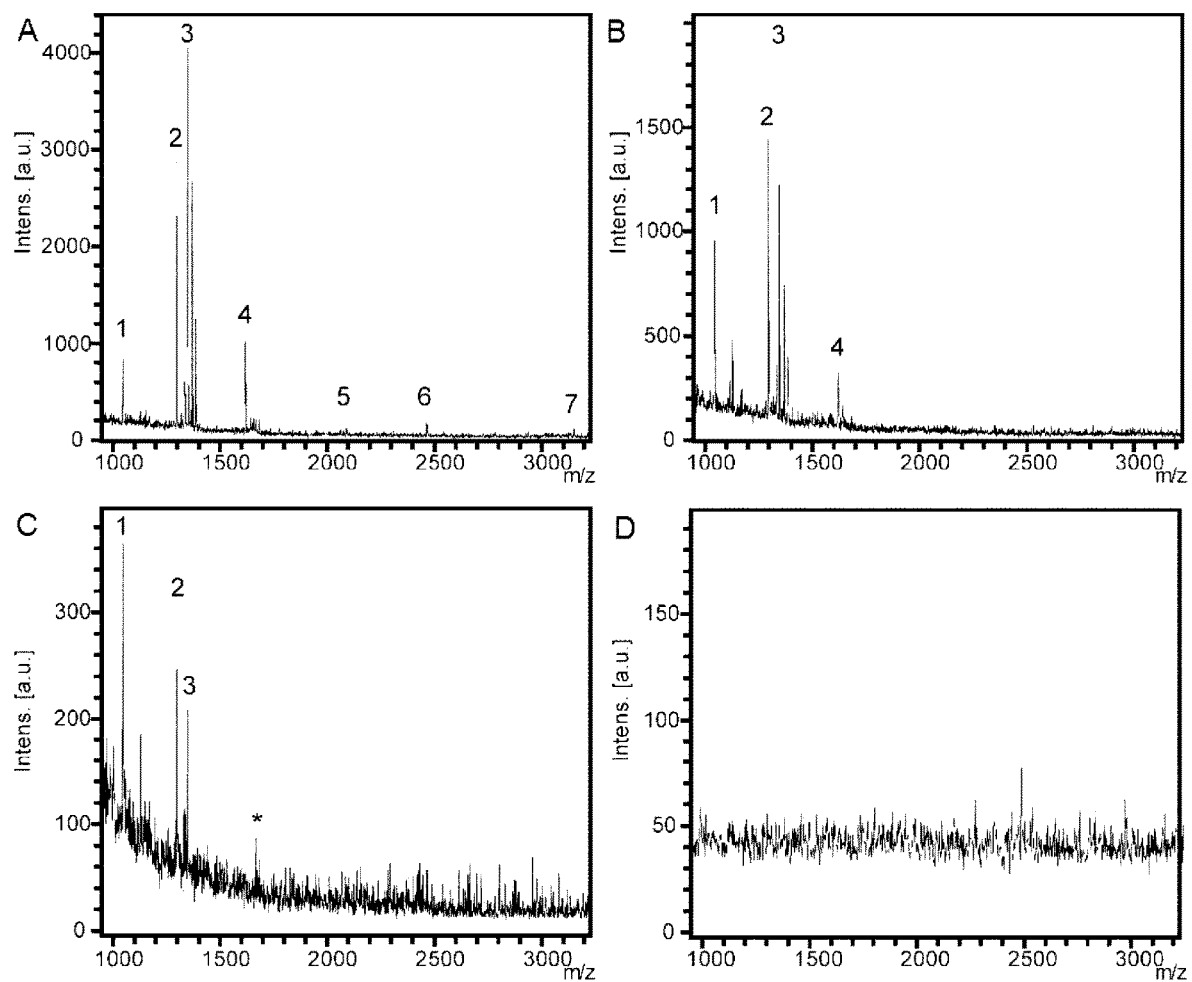
FIG. 15 shows: A-C) Mass spectra collected from SiNP arrays etched for (A) 1 min (450 nm length, aspect ratio of 1.0), (B) 5 min (1360 nm length, aspect ratio of 3.0), and (C) 20 min (3500 nm length, aspect ratio of 7.7), all SiNP arrays had 450 nm diameter and 100 nm spacing and were etched with 4.8 M HF/0.1 M $H_2O_2$ and standard peptide mixture spots were deposited on all surfaces. Peak 1 and 2 correspond to the peptides angiotensin II and I, respectively, while peak 3 corresponds to substance P, peak 4 corresponds to bombecin, peak 5 corresponds to ACTH 1-17, peak 6 corresponds to ACTH 18-39 and peak 7 corresponds to somatostatin. Asterisk (*) corresponds to contamination peaks. (D) SALDI-time-of-fight (TOF) mass spectra collected from a flat silicon surface as a negative control.

The peptide mixture was deposited directly onto the SiNP array surface and allowed to dry. Furthermore, a laser fluence of 70% of the maximum output was used throughout the analysis of the peptides. It was determined that 70% laser fluence was the optimum setting for peptide detection since increasing the fluence resulted in high background noise, while decreasing the fluence resulted in non-optimum signal intensities. SALDI-TOF-MS spectra of the peptide mixture on flat silicon and silicon nanopillar arrays are depicted in FIG. 15.

Figure 16:
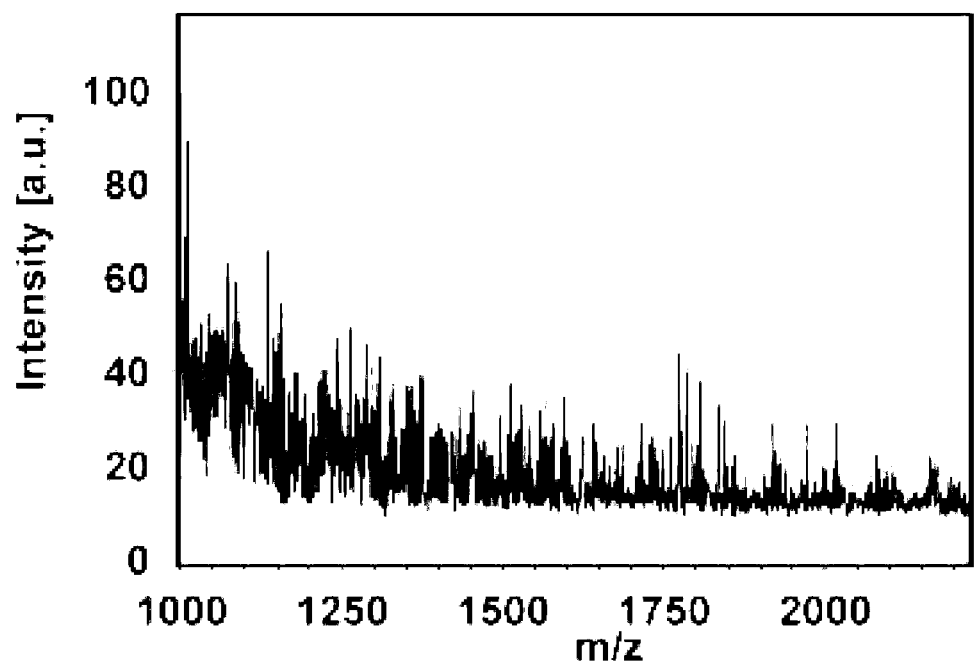
FIG. 16 shows a SALDI-TOF mass spectrum collected of a MilliQ water droplet that did not contain any peptides, wherethe substrate was a SiNP array etched for 1 min using a solution of 4.8 M HF/0.1 M $H_2O_2$.

Mass spectra were collected from SiNP arrays that were etched for 1 min, 5 min, and 20 min (FIGS. 15A, B, and C respectively), and on flat silicon (FIG. 15D) as a negative control. We also performed SALDI-TOF-MS analysis using MilliQ water on a SiNP array etched for 1 min using the same etching conditions described above as a second experimental control (FIG. 16) with no significant peaks appearing above background noise. In previous SALDI-TOF-MS studies, signal-to-noise (S/N) ratios of 3, 4, and 5 were specified as acceptable limits for signal detection (Baumann et al., 2005; Wei et al., 2004; Yao et al., 2008). Here, we chose the S/N ratio ≥3 to indicate successful peptide detection. Peptide peaks could not be observed on the flat silicon surface. In contrast, seven peaks were detected for the sample etched for 1 min, which corresponded to angiotensin II and I (labeled 1 and 2, respectively), substance P (3), bombecin (4), the ACTH clips 1-17 and 18-39 (5 and 6, respectively) and somatostatin (7) as well as two small peaks close to peak 3 which correspond to Na+ and K+ adducts to substance P at +21.98 and +37.95 Da. For the SiNP array, which was etched for 5 min, peaks 5, 6, and 7 were not detected while Na+ and K+ adducts of peak 3 were still being observed. For the sample etched for 20 min, peaks 4, 5, 6, and 7 were not detected at all. In summary, S/N ratios for all analytes decreased with increasing nanopillar length except for angiotensin II where the highest S/N was detected on the 5 min etched SiNP array. The length of the SiNPs affects the distribution of the analyte and their exposure to the nitrogen laser during the SALDI-TOF-MS experiment. Our results suggest that SiNPs with lengths greater than the 1 min etch (450 nm, aspect ratio of 1.0) do not allow effective energy transfer from the laser to the analyte. In longer SiNP arrays, energy transfer from the laser to the analyte may be hindered similar to what has been observed in DIOS for deeper porous layers (Okuno et al., 2005; Piret et al., 2009; Wang et al., 2012). The higher molecular weight peptides in the mixture, ACTH clip 1-17, ACTH clip 18-39, and somatostatin 28 were detected only with short SiNP arrays, which suggests that as the SiNP arrays become longer, they become less efficient in ionising and desorbing molecules with higher molecular weights. Additionally, the 450 nm long SiNP with an aspect ratio of 1.0 outperformed the analyte detection range of commercially available DIOS substrates (MassPREP™ DIOS-target, Waters) where peptides above 2000 Da are not detectable (Shenar et al., 2009). In contrast, we were able to detect ACTH clips 1-17 and 18-39 as well as somatostatin with molecular weights of 2094, 2466, and 3149 Da, respectively.

Example 11—Detection of Methadone by SALDI-TOF-MS Using Ordered SiNP Arrays

Stock solutions of methadone at 0.1 mg/mL were prepared in methanol from a certified standard ampoule and stored at −20° C. Working solutions of 4000 ng/mL were obtained by diluting the stock solutions with MilliQ water. Working solutions were kept at +4° C. and prepared fresh every 2 weeks. Drug solutions at varying concentrations (100-2000 ng/mL) containing the corresponding deutrated internal standard at 500 ng/mL were prepared from working solution immediately prior to analysis.

Aliquots of methadone (1 µL) solutions were deposited onto SiNP array substrates and allowed to completely evaporate. Upon evaporation, SiNP substrates were mounted on a modified MALDI target plate (MTP384, Bruker Daltonics, Germany) using double-sided carbon tape.

Mass spectra were collected using an Autoflex Series III Bruker MALDI-TOF mass spectrometer equipped with a SmartBeam (337 nm, Nd:YAG) 200 Hz pulsed laser, operated at 200 Hz frequency and laser attenuator offset of either 30% (for methadone analysis) or 70% (for peptides analysis) in reflectron positive mode. Mass spectra were generated by averaging 100 individual laser shots per spot, while using 5 spots per surface. This was done in order to minimise the effects of surface-to-surface variations during signal measurement. Data acquisition used flexControl 3.3 (build 85) software and data analysis was performed using flexAnalysis version 3.3. Quadratic external calibration of the TOF tube was performed on the monoisotopic masses of CHCA adducts before each analysis.

The LOD of methadone was measured by establishing the magnitude of contribution from background noise to the analyte signal that was observed. The background noise was calculated by measuring the average signal intensity ratio between the signal intensity at m/z=310 (methadone) and m/z=313 (internal standard, methadone-d3) in the absence of methadone. We averaged eighteen replicates containing methadone-d3 (500 ng/mL) over 3 different SiNP arrays. The LOD for methadone was then defined as three standard deviations above the average background-to-internal standard ratio that was measured.

Figure 17:
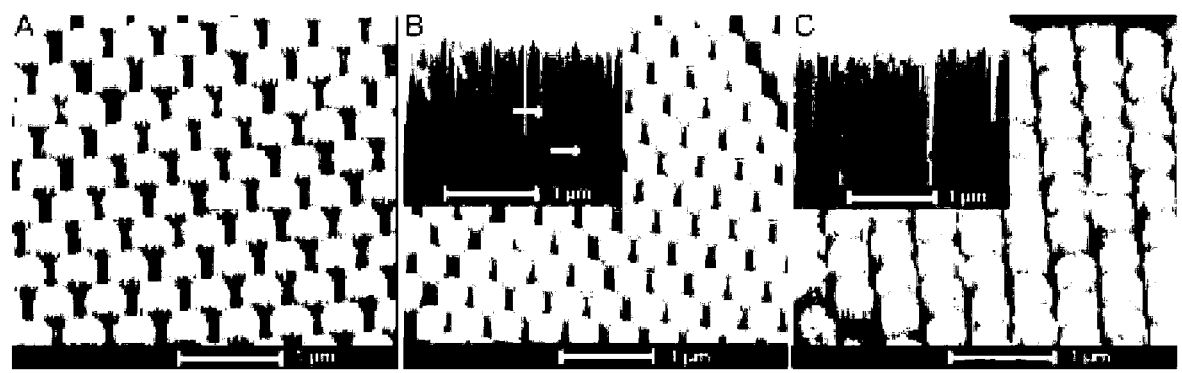
FIG. 17 shows SEM micrographs detailing the effect of increasing $H_2O_2$ concentration on porosity of the SiNPs, when the samples were etched for 1 min with a diameter of 450 nm (aspect ratio of 1.0) in a solution containing 4.8 M HF and (A) 0.1 M $H_2O_2$, (B) 0.2 M $H_2O_2$ and (C) 0.3 M $H_2O_2$, the inset in (B) shows the start of the formation of pores and dents along the SiNP sidewalls as indicated by white arrows, the inset in (C) shows the increased degree of pore and dent formation along the tips and sidewalls of the SiNPs as the concentration of $H_2O_2$ increases.
Figure 18:
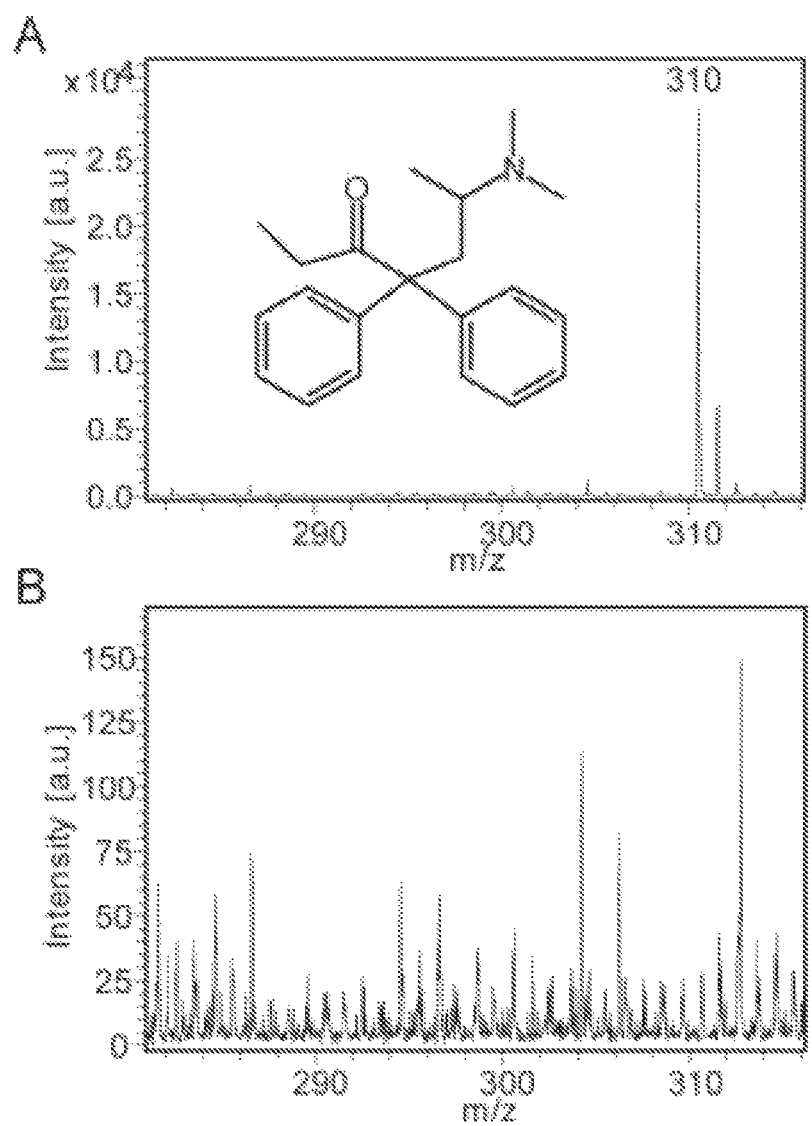
FIG. 18 shows representative SALDI-TOF mass spectra on SiNP arrays etched in a 4.8 M HF/0.1 M $H_2O_2$ solution for 1 min (450 nm in length, 450 nm diameter, 100 nm inter-nanopillar spacing, and an aspect ratio of 1.0) for (A) methadone with a MH+=310 m/z, and (B) MilliQ water as negative control.
Figure 19:
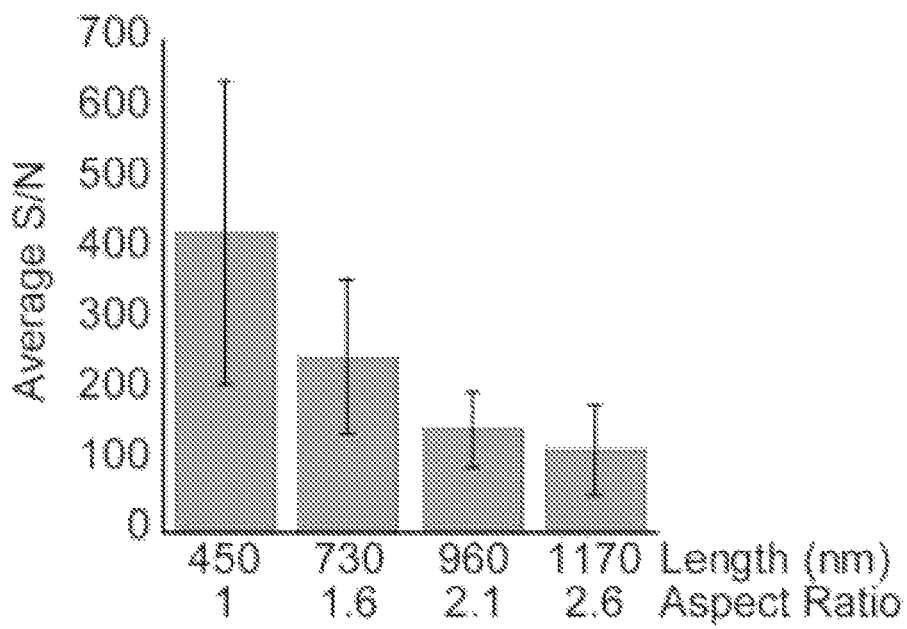
FIG. 19 shows signal-to-noise (S/N) ratios of methadone peaks detected on SiNP arrays, 450 nm in diameter, with different lengths and aspect ratios using SALDI-TOF-MS.

The signal intensity of methadone peaks was tested on SiNP arrays with varying lengths below 1200 nm to fine-tune the SiNP length for highest analytical performance. Average S/N ratios of the methadone peak were used as a quantitative measure for signal intensity in each case. SiNP arrays with lengths measured as 450 (1 min etch, aspect ratio of 1.0), 730 (2 min etch, aspect ratio of 1.6), 960 nm (3 min etch, aspect ratio of 2.1), and 1170 nm (4 min etch, aspect ratio of 2.6) were used in this case. The SiNP arrays were etched using 0.1 M $H_2O_2$, and had diameters of 450 nm according to SEM characterisation (FIG. 17). FIG. 18A shows a representative SALDI mass spectrum for methadone (1000 ng mL$^{-1}$) in water obtained on 450 nm long SiNPs with an aspect ratio of 1.0, which gave the best performance in peptide detection. The quasimolecular ion for methadone (m/z=310) was clearly observed at a S/N of 427.8. In contrast, low signal intensities with no interfering peaks in the mass range for methadone were observed for a background mass spectrum obtained from MilliQ water only (FIG. 18B), note the y-axis scale reduced 200×. A laser fluence of 30% was used in this case since it provided optimum analytical performance and signal intensities.

As in the case with the peptide mixture, the S/N ratio for methadone was seen to decrease with increasing nanopillar length and aspect ratio. This further confirmed the notion that longer SiNPs hinder the process of desorption or attenuate laser irradiation, resulting in non-optimal energy transfer to the analytes.

SALDI-TOF-MS studies of nanostructured surfaces are generally in agreement that high surface roughness leads to increased signal intensity of analytes (Okuno et al., 2005; Finkel et al., 2005). We investigated whether further increasing surface roughness of the SiNPs by introducing structural porosity enhances the signal intensity.

We introduced this porosity in SiNPs by increasing the concentration of $H_2O_2$ in the etching mixture from 0.1 to 0.2 and 0.3 M (Chiappini et al., 2010).

FIG. 17A shows a SiNP array etched in $HF/H_2O_2$ at a concentration of 0.1 M $H_2O_2$. The SiNP tips and sidewalls appeared smooth. Increasing the concentration of $H_2O_2$ during the etching increases the oxidation rate and encourages localised etching along the SiNP walls (Chiappini et al., 2010). When the concentration of $H_2O_2$ was increased to 0.2 M, the sidewalls of the SiNPs began to form cracks and pores perpendicular to the length of the nanopillars in the range of 10-50 nm in size (FIG. 17B). At 0.3 M $H_2O_2$ concentration, this effect became more pronounced and the entire surface of the SiNPs showed increased roughness and enlarged pore sizes between 10 and 200 nm, especially at the tips of the nanopillars and down along the sidewalls (FIG. 17C). The assessment of the effect of SiNP porosity on the S/N ratios during SALDI-MS of methadone is shown in FIG. 20 for three different peroxide concentrations.

Figure 20:
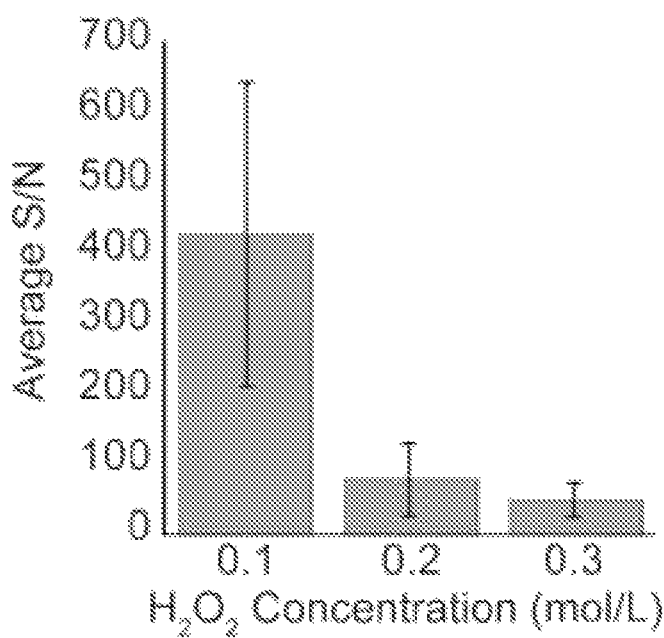
FIG. 20 shows a graph showing the S/N ratios for methadone (1000 ng/mL) analysed on SiNP arrays etched for 1 min (with an aspect ratio of 1.0) at different peroxide concentrations.

In addition to the signal intensity diminishing as a result of longer etching times and hence longer SiNPs, signal intensity also decreased with increasing $H_2O_2$ concentration and hence increasing porosity (FIG. 20). However, the latter effect was more pronounced, showing over 10 fold reduction in S/N from samples etched at 0.1 M $H_2O_2$ to 0.3 M $H_2O_2$. At 1 min etching time, the variation in length and aspect ratios of the SiNPs due to differences in $H_2O_2$ concentrations is negligible (450 nm-500 nm). Therefore, the decrease in signal intensity was mostly attributed to the increase in structural porosity. This reduction in signal intensity relates to the adsorption of analyte molecules inside the cracks and pores shown in FIG. 14, which may actually hinder release of those molecules during laser irradiation. Support for this hypothesis comes from the DIOS literature where small pores sizes in the mesopore range perform poorly in SALDI-TOF-MS (Shen et al., 2000; Xiao et al., 2009; Guinan et al., 2012).

The SiNP arrays etched for 1 min were washed with ethanol and MilliQ water, and reused successfully for the detection of methadone without a noticeable decrease in the observed signal intensity. Furthermore, the same SiNP arrays were stored for up to 3 months under ambient conditions, and then reapplied for SALDI-TOF-MS detection of methadone, while showing no decrease in performance Further investigation of the SiNP arrays using SEM showed no noticeable degradation in structure over time, or with repeated use.

Figure 21:
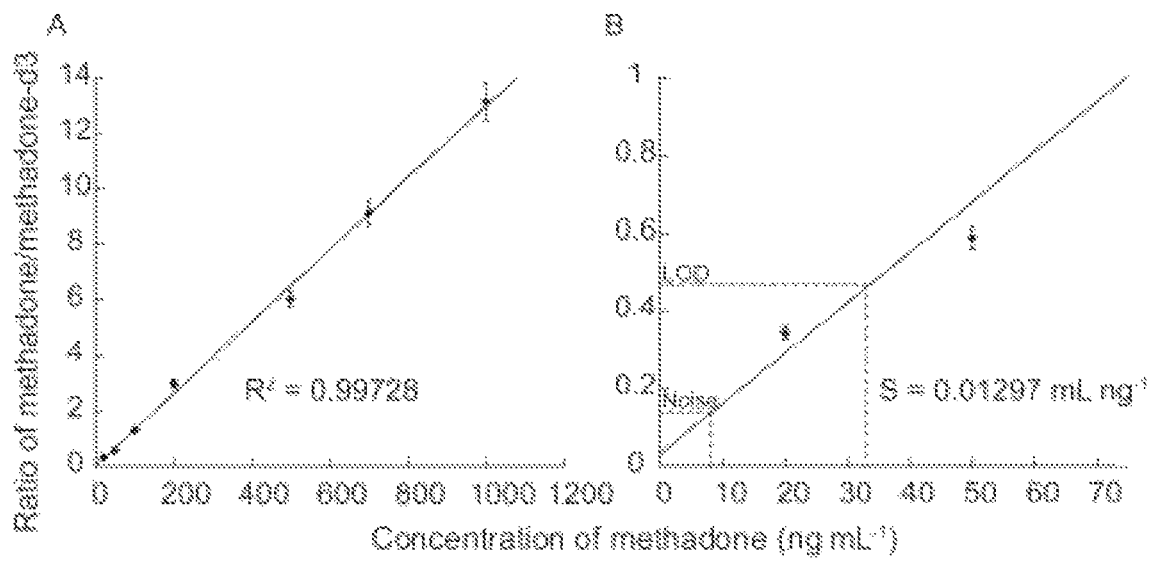
FIG. 21 shows a graph depicting (A) the relationship between the concentration of methadone deposited on a SiNP array etched for 1 min using 4.8 M HF/0.1 M $H_2O_2$ solution and the ratio of the signal detected from the methadone to its deuterated standard fixed at a constant concentration of 500 ng/mL in each of the solutions tested, and (B) a close-up of the lower concentration range with the background noise and the limit of detection (LOD) displayed graphically, as well as the sensitivity calculated from the slope of the line of best fit (S)

The LOD for methadone was evaluated on a SiNP array etched using the conditions, which produced the highest S/N (1 min etching in 4.8 M HF/0.1 M $H_2O_2$, 450 nm length, 450 nm diameter, and aspect ratio of 1.0). A deuterated standard of methadone was introduced as an internal standard at a constant concentration of 500 ng/mL. The LOD for methadone was investigated over the concentration range. The laser fluence was set to a fixed value of 30% while measuring the signal from each concentration. Methadone detection showed good linearity ($R^2>0.99$) in the signal intensity ratio of drug to internal standard over the concentration range of 0-2000 ng/mL, demonstrating that quantification of these compounds using SiNP arrays can be achieved (FIG. 21A). An LOD value of 32 ng/mL was obtained. FIG. 21B shows a close-up of the 0-70 ng/naL concentration range, showing that the LOD was determined as three times the noise level. The sensitivity (S) was calculated as the slope of the line of best fit and was defined as the signal ratio of (methadone/methadone-d3) per ng/mL. Given that the signal ratio has arbitrary units, S=0.013 absorbance units per ng/mL or 0.013 mL/ng.

Example 12—Deposition of Saliva Samples on pSi Substrates

Oral fluids were obtained according to the EWDTS guidelines (Cooper et al., 2011) from a drug-free volunteer, and stored in the cold before use for no longer than 1 week. 40 mL of neat saliva samples was spiked with 10 mL of a solution containing both drugs and internal standards to give a final concentration in the range 10-200 ng/mL for MA, MDMA and cocaine and 100 ng/mL for the internal standards. Ammonium bicarbonate buffer (1 mL, 1 M) was subsequently added to the spiked saliva and 2 mL of the resulting solution was deposited onto a silane-coated pSi substrate prepared according to Example 8 and silane-coated using $F_5PhPr$. The sample was allowed to interact with the surface for 5 min in order to facilitate extraction. The drop was finally washed away by adding 10 mL of 10 mM ammonium phosphate, pipetting a few times and discarding the solution.

Example 13—Detection of Methadone on pGe Substrates

It has previously been reported that pGe can be fabricated via bipolar electrochemical etching (BEE) technique using HF or HCl as the electrolyte, with cathodisation followed by an anodisation step that results in pore formation. Cathodisation serves to protonate Ge—Ge bonds, subsequently creating a hydride terminated internal surface (Fang et al., 2007, Tutashkonko et al., 2013).

Here, the present inventors report on the fabrication of oxidised mesoporous p-type germanium for the detection of methadone using SALDI-MS for the first time. Unlike oxidised pSi, which is hydrophilic in nature, oxidised pGe substrates are hydrophobic owing to the hydroxyl monolayer on Ge compared with the hydrated oxide present for pSi (Chazalviel et al., 2004). This allows the direct application of pGe as SALDI substrates without silanisation techniques that may be associated with pSi based SALDI substrates to render the substrate hydrophobic. pGe was fabricated using BEE of p-type germanium wafers (Tutashkonko et al., 2013). Subsequently, the pGe substrates were functionalised and used as a SALDI-MS substrate for the detection of methadone.

Reagents

Ethanol (99.9%) and HF (48%) were purchased from Chem Supply (SA, Australia). Water was purified using a Millipore Q-Pod system (Merck, Darmstadt, Germany). $F_{13}$ was purchased from Gelest Inc. (PA, USA). Certified standards of methadone (1 mg/mL) were kindly provided by Forensic Science South Australia (SA, Australia).

Fabrication of pGe

Electrochemical etching of germanium was conducted using 0.3 mm thick highly Ga doped p-type germanium wafers with a resistivity of <0.0020 Ohm cm and (1 0 0) orientation provided by Umicore®. The fabricated substrates were cleaned prior to conducting experiments for 5 min in milliQ acetone, ethanol, and then were immediately dried under nitrogen gas flow. A homemade, one-side, O-ring type Teflon cell of 10 mm in diameter with Pt mesh electrode as a counter electrode was used. 48% aqueous HF was used as an electrolyte.

The BEE anodisation of the germanium wafer was carried out under galvanostatic conditions using a programmable Keithley® current source meter. A current density of 0.5-1.5 mA/cm$^2$ in 48% HF was applied in the form of rectangular wave with the same amplitude of positive (anodic) and negative (cathodic) pulses for 1 and 2 s, respectively. The prepared samples were rinsed in ethanol then dried in air for 5 min to ensure slow evacuation of EtOH from the pores, and then under a stream of nitrogen.

Functionalisation of pGe

The freshly etched pGe was rinsed with ethanol and dried under nitrogen. Subsequently, pGe substrates were immersed in MilliQ water for 30 s and used for SALDI-MS analysis.

For silanisation of pGe, freshly etched pGe was ozone oxidised at a flow rate of 3.25 g/h using an Ozone-Generator 500 (Fischer, Germany) for 30 min and then neatly silanised with $F_{13}$ for 15 min at 90° C.

Preparation of Drug Solutions

Stock solutions of methadone at 0.01 mg/mL were prepared in ethanol from certified standards (1 mg/mL). Solutions were stored at −20° C. Working solutions of 1000 ng/mL were obtained by diluting the stock solutions with water. Working solutions were stored at +4° C. and prepared fresh every 2 weeks.

Sample Deposition Method for Illicit Drug Solutions in Water

Aliquots of drug solutions (1 µL) were deposited onto pGe surfaces. The solvent was allowed to completely evaporate. Upon evaporation, pGe chips were mounted on a modified MALDI target plate (MTP384, Bruker Daltonics, Bremen, Germany) and analysed.

SALDI-MS Analysis

Mass spectra were collected using an ultrafleXtreme Bruker MALDI-TOF-TOF mass spectrometer equipped with a SmartBeam (337 nm, Nd:YAG) 2 kHz pulsed laser, operated at 2 kHz, and laser attenuator offset of 10% in reflectron positive mode. Mass spectra were generated by averaging 500 individual laser shots. Data acquisition used flexControl 3.4 (build 78) software and data analysis was performed using flexAnalysis version 3.4. Instrumental parameters for the RP acquisition were set as follows: 19.00 and 16.80 kV for ion sources 1 and 2, respectively, 8.25 kV for the lens and 21.00 and 9.40 kV for reflectors 1 and 2, respectively. Quadratic external calibration of the TOF tube was performed prior to each acquisition on the monoisotopic masses of CsI.

Scanning Electron Microscopy (SEM) Analysis

SEM imaging and characterisation were performed using a Quanta 450 FEG Environmental SEM (FEI, Netherlands) fitted with an SSD detector and operated at 30 kV. Length measurements were performed using the SEM's operating software.

Results and Discussion

Figure 22:
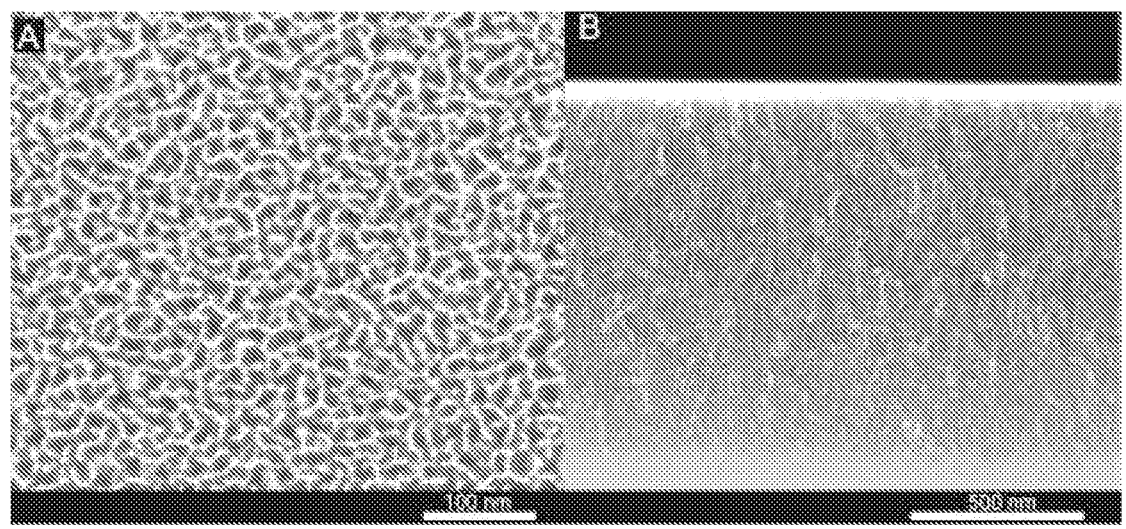
FIG. 22 shows SEM micrographs depicting average pGe (A) pore size and (B) pore depth on pGe substrates.

Surface characterisation of the surface morphology was performed using SEM as displayed in FIG. 22. pGe substrates had pore sizes of approximately 12 nm (FIG. 22A) and pore depths of 1.7 µm (FIG. 22B).

Figure 23:
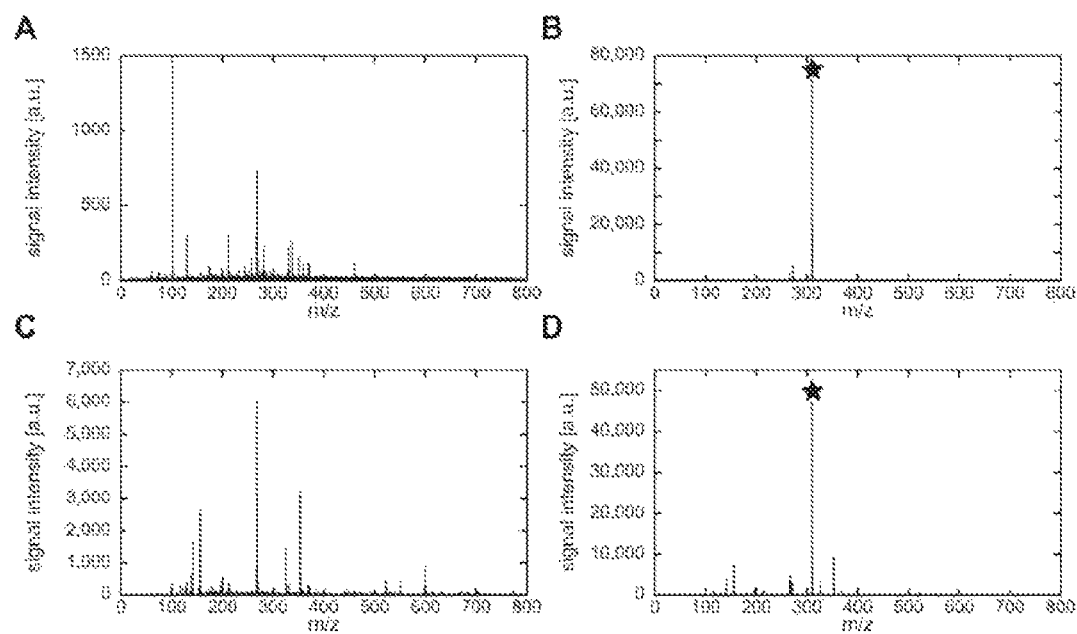
FIG. 23 shows graphs depicting exemplary background mass spectra observed for functionalised pGe substrates treated using (A) MilliQ, and (C) $F_{13}$, respectively, and spectra observed for methadone (1000 ng/mL) on pGe substrates treated using (B) MilliQ and (D) $F_{13}$, respectively.

FIG. 23 displays mass spectra observed for functionalised pGe substrates. For pGe substrates treated with MilliQ water (FIG. 23A), low intensity background spectra were observed. However, for $F_{13}$ silanised pGe a high intensity background spectrum was observed (FIG. 23C). Each of the functionalised substrates were investigated for the detection of methadone in water at a concentration of 1000 ng/mL. FIG. 23B displays the spectrum observed for methadone on the MilliQ water treated pGe substrates. A high intensity mass spectrum with low intensity background peaks was observed for the detection of methadone (m/z 310) in water (FIG. 23B). Similarly, high intensity peaks for $F_{13}$ functionalised pGe were observed for the detection of methadone (FIG. 23D).

These results demonstrate the detection of methadone using pGe substrates oxidised with $H_2O$ and perfluorinated silanes Example 13—Ag Internal Calibrants for High Mass Accuracy Imaging Mass Spectrometry of Small Molecules DIOS chips functionalised with $F_{13}$ (described in Example 8) were sputter coated with either 0.4, 0.7, 1.7 or 3.4 nm thick Ag layers. Ag-coated DIOS substrates were prepared by using a Q300T-D sputter coater equipped with a quartz crystal microbalance (QCM) (Quorom Technologies, United Kingdom). Ag of 99.9999% purity was used. The QCM was calibrated prior to Ag deposition to give a tooling factor of 8.5. QCM measurements were performed during sputtering to estimate layer thickness. Coatings were as follows: i) QCM: 0.4 nm, current: 6 mA, time: 3 s, ii) QCM: 0.7 nm, current: 6 mA, time: 6 s, iii) QCM: 1.7 nm, current: 50 mA, calibrated using Au, time: 4 s and iv) QCM: 3.2 nm, current: 50 mA. The Ag coating was used as an internal calibrant, specifically, 10 Ag clusters were used as internal calibrants. The masses used for calibration were $Ag_1$ (106.904548), $Ag_2$ (m/z 213.809645), $Ag_3$ (m/z 320.714742), $Ag_4$ (m/z 431.619149), $Ag_5$ (m/z 538.524246), $Ag_6$ (m/z 647.428998), $Ag_7$ (m/z 754.334095), $Ag_8$ (m/z 863.238847), $Ag_9$ (m/z 970.143944) and $Ag_{10}$ (m/z 1079.048696).

Figure 24A:
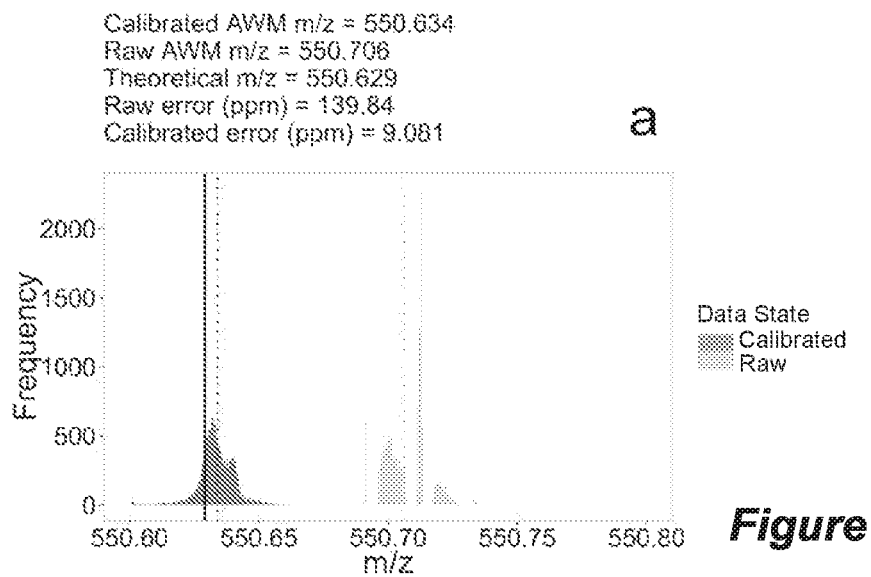
FIG. 24 shows data sourced from mass spectrometry imaging analysis of a native fingerprint deposited on a DIOS chip coated with a 1.7 nm thick Ag layer, with histograms of raw peaks (dark grey; left) and internally re-calibrated peaks (light grey; right) of all peaks within the m/z ranges (A) 550.600-550.800 and (D) 827.610-827.910, dotted lines indicate AWM m/z values and solid lines indicate true theoretical m/z values, and provided with each histogram are the corresponding calibrated abundance weighted mean (AWM) m/z, raw AWM m/z, theoretical m/z as well as the raw and calibrated errors (ppm) for the AWMs relative to the theoretical m/z; and mass deviation heat maps are shown for the fingerprints in 550.600-550.800 m/z range for (B) calibrated and (C) raw data; and for the m/z range 827.610-827.910 in (E) calibrated and (F) raw data, where mass deviations are determined by the difference between detected peak m/z and the theoretical m/z scaled from −0.22 (darker) through to 0 (white, equal to theoretical m/z) and +0.22 m/z (darker).
Figure 24B:
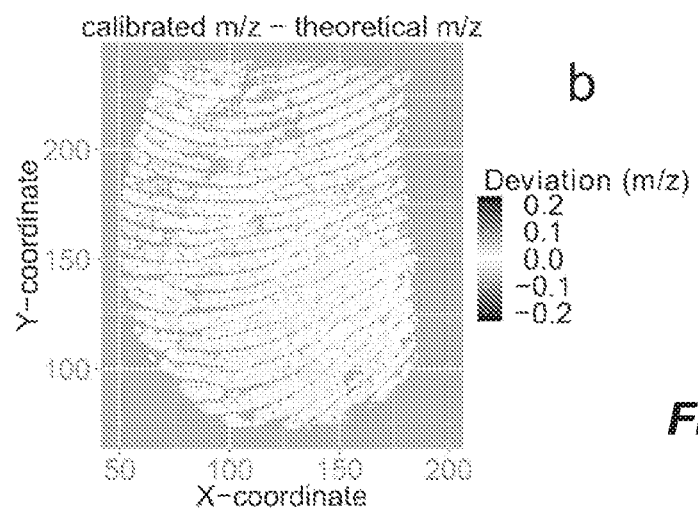
Figure 24C:
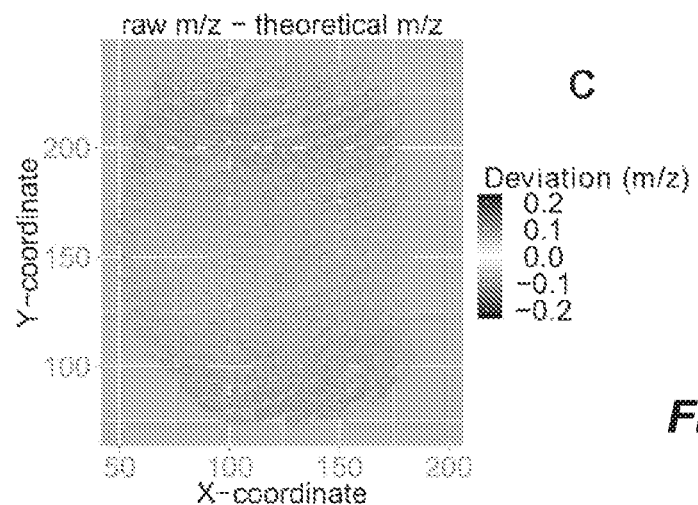
Figure 24D:
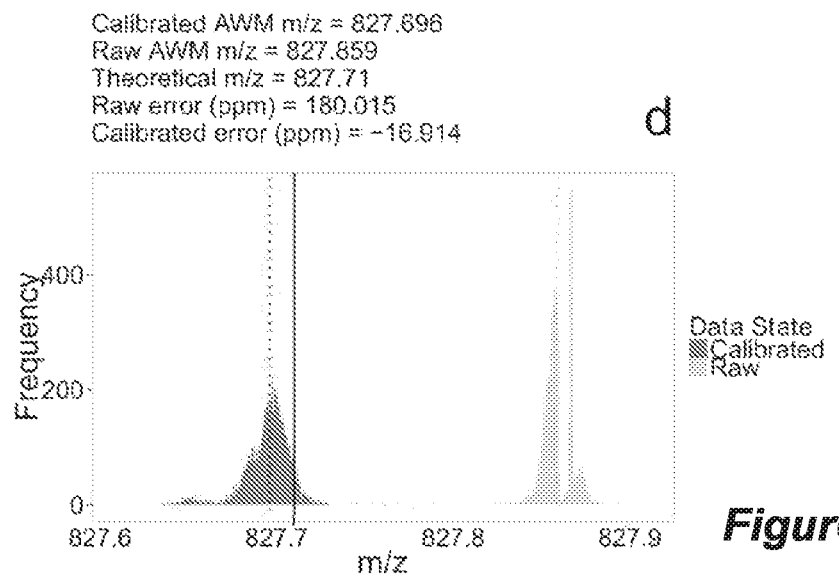
Figure 24E:
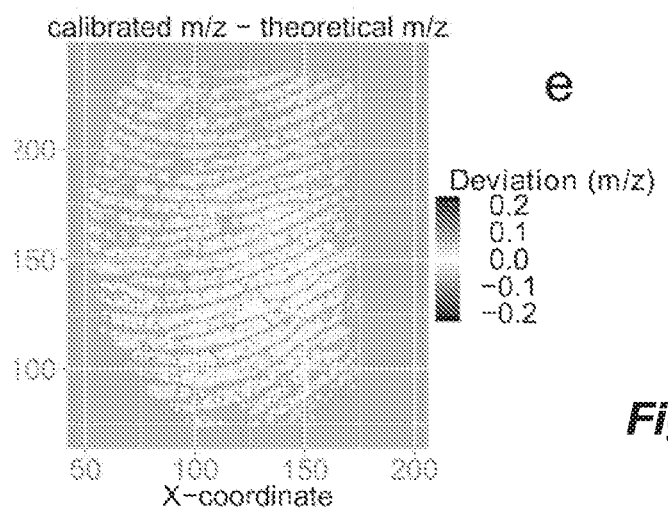
Figure 24F:
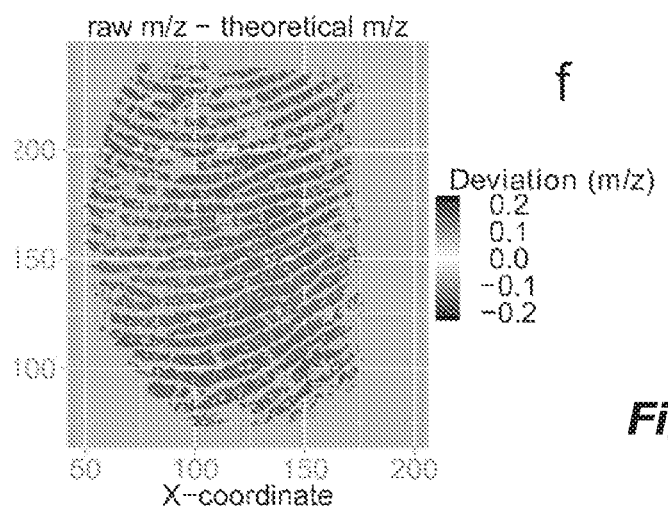

Fingermarks were deposited and imaged on the Ag-coated DIOS chips and an increase in mass accuracy was demonstrated in the low mass range following internal recalibration. As an example, the effect of the calibration is further demonstrated in FIG. 24 for two fingerprint analytes deposited on a DIOS chip coated with a 1.7 nm thick Ag layer. FIGS. 24A and 24D display m/z histograms for all raw (dark grey; left) and internally calibrated (light grey; right) peaks in the m/z ranges 550.600 to 550.800 and 827.610 to 827.910, respectively. The raw histograms exhibit the same broad distribution with multiple mass clusters, which are homogenized and substantially shifted following calibration. The AWM m/z values for both the raw and calibrated peaks within the assigned m/z ranges are presented in FIGS. 24A and 24D. In addition, these AWM m/z values are plotted on the histograms as dotted lines, with the theoretical m/z of the candidate compound indicated by a solid black line. When compared to the theoretical m/z, internal calibration causes an absolute reduction in ppm error from 139.84 to 9.081 for calibrated AWM m/z 550.634 (FIG. 24A) and a reduction from 180.015 to 16.914 for calibrated AWM m/z 827.696 (FIG. 24D). This amounts to an error reduction of 15.40 and 10.64 times, respectively. FIG. 24 also presents spatial mass error maps for the m/z values within the m/z ranges 550.600 to 550.800 for calibrated (FIG. 24B) and raw (FIG. 24C) data; and 827.610 to 827.910 for calibrated (FIG. 24E) and raw (FIG. 24F) data. The intensity scale of −0.22 to 0 to +0.22 is centered on the assigned theoretical m/z value, and, as indicated by the histogram, the raw mass error maps (FIGS. 24C and 24F) show the significant positive error prior to calibration. In sharp contrast, the m/z values plotted in the calibrated maps (FIGS. 24B and 24E) cluster tightly around the theoretical m/z and the maps are thus almost completely white. Histograms were produced in R using all peaks picked for each exported spectrum across the entire acquired imaging data set. Accordingly, the method presented here provides a widely accessible solution for high mass accuracy SALDI-TOF/TOF MS of small molecules in both single measurement and mass spectrometry imaging formats.

Mass spectra were collected using an ultrafleXtreme MALDI-TOF/TOF mass spectrometer, equipped with a SmartBeam (337 nm, Nd:YAG) 2 kHz pulsed laser, operated in reflectron positive mode in the mass range m/z 20-1500 (Bruker Daltonics, Bremen, Germany). Data acquisition used flexControl 3.4.78 software and initial data analyses were performed using flexImaging 3.4. The laser power was user-optimized, as required, for each Ag-coated DIOS substrate investigated. Pre-calibration was performed prior to main IMS data acquisition.

Spectra were processed in flexAnalysis (version 3.4, Bruker Daltonics). Settings were as follows: centroid peak picking with signal-to-noise threshold: 5, smoothing: Savitzky-Golay 0.02 m/z, baseline subtraction: TopHat. Peak lists were processed with and without cubic-enhanced internal re-calibration. The re-calibration used a custom Ag cluster/isotopomer list using internal calibrants $Ag_1$-$Ag_{10}$. Peak lists were exported to text files (ASCII), containing the m/z, intensity, resolution, signal-to-noise ratio (S/N) and area, using a custom flexAnalysis script generously provided by Bruker Daltonics. Peak lists were further processed using an in-house R script (Tam, 2014) using open source software, which produced combined data frames as well as histograms and mass deviation maps. Histograms, abundance weighted mean (AWM) m/z values and errors were calculated using all data in selected m/z ranges.

REFERENCES

S. Baumann, U. Ceglarek, F. Georg Martin, J. Lembcke, et al. Clin. Chem., 51 (2005) 973-80.
C. Chiappini, X. Liu, J. R. Fakhoury, M. Ferrari. Adv. Funct. Mater., 20 (2010) 2231-2239.
Cooper G, Moore C, George C, Pichini S. Guidelines for European workplace drug testing in oral fluid. Drug testing and analysis. 2011; 3(5):269-76. doi:10.1002/dta.284.
J. N. Chazalviel, F. Maroun, F. Ozanam, An Interface-Free-Energy Approach to Semiconductor Electrode Chemistry Examples of Si and Ge. Journal of The Electrochemical Society, (2004) 151(2): E51-E55.
C. Fang, et al., Electrochemical pore etching in Ge—An overview. Physica status solidi (a) (2007) 204(5): 1292-1296.
N. H. Finkel, B. G. Prevo, O. D. Velev, L. He. Anal. Chem., 77 (2005) 1088-1095.
Gu L, Park J-H, Duong K H, Ruoslahti E, Sailor M J. Small. 2010; 6(22):2546-52. doi:10.1002/smll.201000841.
T. Guinan, M. Ronci, H. Kobus, N. H. Voelcker. Talanta, 99 (2012) 791-798.
Z. Huang, N. Geyer, P. Werner, J. de Boor and U. Gösele, Advanced Materials, 2011, 23, 285-308.
T. R. Northen, H.-K. Woo, M. T. Northen, A. Nordström, W. Uritboonthail, K. L. Turner, G. Siuzdak. J. Am. Soc. Mass Spectrom., 18 (2007) 1945-1949.
S. Okuno, R. Arakawa, K. Okamoto, Y. Matsui, S. Seki, T. Kozawa, S. Tagawa, Y. Wada. Anal. Chem., 77 (2005) 5364-5369.
G. l. Piret, H. Drobecq, Y. Coffinier, O. Melnyk, R. Boukheroub. Langmuir, 26 (2009) 1354-1361
M. Ronci, D. Rudd, T. Guinan, K. Benkendorff, N. H. Voelcker. Anal. Chem., 84 (2012) 8996-9001.
Saferstein in "Forensic Science Handbook", Vol. II (2nd Edition) Prentice Hall; 2 edition (2004).
Z. Shen, J. J. Thomas, C. Averbuj, K. M. Broo, M. Engelhard, J. E. Crowell, M. G. Finn, G. Siuzdak. Anal. Chem., 73 (2000) 612-619.
N. Shenar, S. Cantel, J. Martinez, C. Enjalbal. Rapid Commun. Mass Spectrom., 23 (2009) 2371-2379.
R. C. Team. R Foundation for Statistical Computing: Vienna, Austria, 2014.
Tutashkonko, et al. Electrochimica Acta, (2013) 88: 256-262
C. Wang, J. M. Reed, L. Ma, Y. Qiao, Y. Luo, S. Zou, J. J. Hickman, M. Su. J. Phys. Chem. C, 116 (2012) 15415-15420.
H. Wei, K. Nolkrantz, D. H. Powell, J. H. Woods, M.-C. Ko, R. T. Kennedy. Rapid Commun. Mass Spectrom., 18 (2004) 1193-1200.
Y. Xiao, S. T. Retterer, D. K. Thomas, J.-Y. Tao, L. He. J. Phys. Chem. C, 113 (2009) 3076-3083.
N. Yao, H. Chen, H. Lin, C. Deng, X. Zhang. J. Chromatogr. A, 1185 (2008) 93-101.

The reference to any prior art in this specification is not, and should not be taken as, an acknowledgement of any form of suggestion that such prior art forms part of the common general knowledge.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. An in vitro method for detecting one or more target low molecular weight analyte(s) in a biological fluid, the method comprising introducing etched porous germanium (pGe) microparticles (MPs) into a biological fluid suspected of containing the target low molecular weight analyte(s) under conditions to allow the pGe MPs to capture at least some of the target low molecular weight analyte(s) when present from the biological fluid, and analysing the pGe MPs by surface-assisted laser desorption/ionisation (SALDI) mass spectrometry to detect the target low molecular weight analyte(s) when present, wherein the pGe MPs are prepared by electrochemical etching.

2. The method according to claim 1, wherein the surface of the pGe MPs further comprises a fluorinated silane coating.

3. The method according to claim 1, wherein the target analyte is selected from the group consisting of opiates, amphetamines, benzodiazapines, and tropane alkaloids.

4. The method according to claim 1, wherein the method further comprises spiking the sample of the biological fluid with a solution containing specific target analytes of interest and an internal standard to give a spiked sample with a final concentration of target analytes in the range of from about 1 ng/mL to about 1000 ng/mL per target analyte and a final concentration of internal standard of about 50 ng/mL to about 150 ng/mL.

5. The method according to claim 1, wherein the pGe is coated with a coating layer that provides an internal calibrant.

* * * * *